United States Patent
Bolton et al.

[11] Patent Number: 5,919,780
[45] Date of Patent: Jul. 6, 1999

[54] TRICYCLIC INHIBITORS OF PROTEIN FARNESYLTRANSFERASE

[75] Inventors: Gary L. Bolton; Annette M Doherty; James S. Kaltenbronn; John Quin, III, all of Ann Arbor; Jeffrey D. Scholten, Brighton; Judith Sebolt-Leopold, Ann Arbor, all of Mich.; Harold Zinnes, Lake Worth, Fla.

[73] Assignee: Warner Lambert Company, Morris Plains, N.J.

[21] Appl. No.: 08/981,505

[22] PCT Filed: Jun. 4, 1996

[86] PCT No.: PCT/US96/08528

§ 371 Date: Dec. 11, 1997

§ 102(e) Date: Dec. 11, 1997

[87] PCT Pub. No.: WO97/00252

PCT Pub. Date: Jan. 3, 1997

Related U.S. Application Data

[60] Provisional application No. 60/000,913, Jun. 16, 1995.

[51] Int. Cl.$^6$ .................................................. A01N 43/62
[52] U.S. Cl. ..................... 514/220; 540/586; 540/587; 540/557; 540/578
[58] Field of Search ................................ 540/586, 587, 540/557, 578; 514/220

[56] References Cited

FOREIGN PATENT DOCUMENTS

| 980 853 | 8/1961 | United Kingdom . |
| 980853 | 8/1961 | United Kingdom . |
| 9510516 | 4/1995 | WIPO . |

OTHER PUBLICATIONS

Chem. Abst., vol. 64, 1966., 8220 e pp. 8220–8222.
Kohl et al., Nature Medicine, vol. 1, No. 8, Aug. 1995, pp. 792–797.
Glenn et al., Science, vol. 256, May 29, 1962, pp. 1331–1332.
International Search Report for International Application No. PCT/US96/08528, mailed on Sep. 2, 1996.

*Primary Examiner*—Mukund J. Shah
*Assistant Examiner*—Pavanaram K Sripada
*Attorney, Agent, or Firm*—Francis J. Tinney; Evelyn D. Shen

[57] ABSTRACT

Compounds of formula I

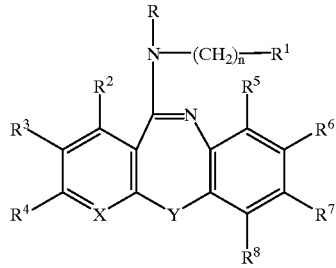

wherein X is N or C—$R^9$,
Y is N—$R^{10}$, $CH_2$, O, S, SO, $SO_2$, C=O or CH—OH,
R is H or alkyl,
$R^1$ is heteroaryl,
n is 1–5, and
$R^2$–$R^{10}$ are H or various substituents,
are useful as inhibitors of protein farnesyl transferase and for the treatment of proliferative diseases including cancer, restenosis and psoriasis, and as antiviral agents.

13 Claims, No Drawings

TRICYCLIC INHIBITORS OF PROTEIN FARNESYLTRANSFERASE

This application claims benefit of provisional application Ser. No. 60/000,913 filed Jun. 16, 1995.

BACKGROUND OF THE INVENTION

The present invention relates to novel tricyclic compounds useful as pharmaceutical agents, to methods for their production, to pharmaceutical compositions which include these compounds and a pharmaceutically acceptable carrier, and to pharmaceutical methods of treatment. The novel compounds of the present invention inhibit farnesyltransferase enzyme which activates ras proteins which in turn activate cellular division. More particularly, the novel compounds of the present invention are useful in the treatment of proliferative diseases such as, for example, cancer, restenosis, and psoriasis, and as antiviral agents.

Ras protein (or p21) has been examined extensively because mutant forms are found in 20% of most types of human cancer and greater than 50% of colon and pancreatic carcinomas (Gibbs J. B., Cell, 65:1 (1991), Cartwright T., et al., Chimica. Oggi., 10:26 (1992)). These mutant ras proteins are deficient in the capability for feedback regulation that is present in native ras and this deficiency is associated with their oncogenic action since the ability to stimulate normal cell division can not be controlled by the normal endogenous regulatory cofactors. The recent discovery that the transforming activity of mutant ras is critically dependent on post-translational modifications (Gibbs J., et al., Microbiol. Rev., 53:171 (1989)) has unveiled an important aspect of ras function and identified novel prospects for cancer therapy.

In addition to cancer, there are other conditions of uncontrolled cellular proliferation that may be related to excessive expression and/or function of native ras proteins. Post-surgical vascular restenosis is such a condition. The use of various surgical revascularization techniques such as saphenous vein bypass grafting, endarterectomy and transluminal coronary angioplasty is often accompanied by complications due to uncontrolled growth of neointimal tissue, known as restenosis. The biochemical causes of restenosis are poorly understood and numerous growth factors and protooncogenes have been implicated (Naftilan A. J., et al., Hypertension, 13:706 (1989) and J. Clin. Invest., 83:1419; Gibbons G. H., et al., Hypertension, 14:358 (1989); Satoh T., et al., Mollec. Cell. Biol., 13:3706 (1993)). The fact that ras proteins are known to be involved in cell division processes makes them a candidate for intervention in many situations where cells are dividing uncontrollably. In direct analogy to the inhibition of mutant ras related cancer, blockade of ras dependant processes has the potential to reduce or eliminate the inappropriate tissue proliferation associated with restenosis, particularly in those instances where normal ras expression and/or function is exaggerated by growth stimulatory factors.

Ras functioning is dependent upon the modification of the proteins in order to associate with the inner face of plasma membranes. Unlike other membrane-associated proteins, ras proteins lack conventional transmembrane or hydrophobic sequences and are initially synthesized in a cytosol soluble form. Ras protein membrane association is triggered by a series of post-translational processing steps that are signaled by a carboxyl terminal amino acid consensus sequence that is recognized by protein farnesyltransferase (PFT). This consensus sequence consists of a cysteine residue located four amino acids from the carboxyl terminus, followed by two lipophilic amino acids and the C-terminal residue. The sulfhydryl group of the cysteine residue is alkylated by farnesylpyrophosphate in a reaction that is catalyzed by protein farnesyltransferase. Following prenylation, the C-terminal three amino acids are cleaved by an endoprotease and the newly exposed alpha-carboxyl group of the prenylated cysteine is methylated by a methyl transferase. The enzymatic processing of ras proteins that begins with farnesylation enables the protein to associate with the cell membrane. Mutational analysis of oncogenic ras proteins indicate that these post-translational modifications are essential for transforming activity. Replacement of the consensus sequence cysteine residue with other amino acids gives a ras protein that is no longer farnesylated, fails to migrate to the cell membrane and lacks the ability to stimulate cell proliferation (Hancock J. F., et al., Cell, 57:1167 (1989), Schafer W. R., et al., Science, 245:379 (1989), Casey P. J., Proc. Natl. Acad. Sci. USA, 86:8323 (1989)).

Recently, protein farnesyltransferases (PFTs, also referred to as farnesyl proteintransferases (FPTs) have been identified and a specific PFT from rat brain was purified to homogeneity (Reiss Y., et al., Bioch. Soc. Trans., 20:487–88 (1992)). The enzyme was characterized as a heterodimer composed of one alpha-subunit (49 kDa) and one beta-subunit (46 kDa), both of which are required for catalytic activity. High level expression of mammalian PFT in a baculovirus system and purification of the recombinant enzyme in active form has also been accomplished (Chen W.-J., et al., J. Biol. Chem., 268:9675 (1993)).

In light of the foregoing, the discovery that the function of oncogenic ras proteins is critically dependent on their post-translational processing provides a means of cancer chemotherapy through inhibition of the processing enzymes. The identification and isolation of a protein farnesyltransferase that catalyzes the addition of a farnesyl group to ras proteins provides a promising target for such intervention. Recently, it has been determined that prototypical inhibitors of PFT can inhibit ras processing and reverse cancerous morphology in tumor cell models (Kohl N. E., et al., Science, 260:1934 (1993), James G. L., et al., Science, 260:1937 (1993), Garcia A. M., et al., J. Biol. Chem., 268:18415 (1993)). Furthermore, Blaskovich M., et al., "Proceedings Eighty-Sixth Annual Meeting American Association For Cancer Research," Mar. 18–22, 1995, Toronto, Ontario, Canada, Vol. 86, March 1995, Abstract 2578, disclosed a series of tetrapeptide inhibitors of farnesyltransferase which inhibited growth of tumor cells in nude mice.

Nagasu T., et al., "Proceedings Eighty-Sixth Annual Meeting American Association For Cancer Research," Mar. 18–22, 1995, Toronto, Ontario, Canada, Vol. 86, March 1995, Abstract 2615, disclosed a peptidomimetic inhibitor, B956, of farnesyltransferase which inhibits growth of human tumor xenografts in nude mice. Inhibition of tumor growth is correlated with inhibition of ras processing.

Thus, it is possible to prevent or delay the onset of cellular proliferation in cancers that exhibit mutant ras proteins by blocking PFT. By analogous logic, inhibition of PFT would provide a potential means for controlling cellular proliferation associated with restenosis, especially in those cases wherein the expression and/or function of native ras is overstimulated.

PCT Published Patent Application WO91/16340 discloses cysteine containing tetrapeptide inhibitors of PFT of the Formula CAAX.

PCT Published Patent Application WO94/26723 discloses a series of benzodiazepine derivatives as inhibitors of ras farnesyl:proteintransferase.

British Published Patent Application UK 980,853 disclosed compounds of the formula:

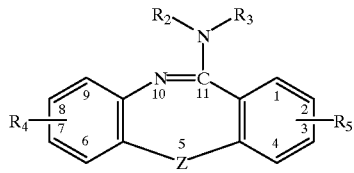

and acid addition salts and quaternary ammonium derivatives thereof, in which:

Z represents a sulphur atom or a sulphoxide group (—SO—) or an amino group of the formula —(N—$R_1$)—, wherein $R_1$ represents a hydrogen atom or a protecting group, e.g., an acyl or a benzyl group, or an alkyl or alkenyl group containing up to 5 carbon atoms;

$R_2$ and $R_3$, which may be the same or different, represent hydrogen atoms, or alkyl or alkenyl groups containing up to 5 carbon atoms, amino groups, monoalkylamino or dialkylamino groups, monoalkylaminoalkyl or dialkylaminoalkyl groups or monocyclic aryl or aralkyl groups, which aryl or aralkyl groups may be substitued with halogen atoms, trifluoromethyl groups, hydroxy groups or alkyl groups, alkoxy groups or alkylmercapto groups containing from 1 to 3 carbon atoms, or may together with the adjacent nitrogen atom form a cycloalkylamino group which may contain further heteroatoms, which heteroatoms, if nitrogen, may carry hydrogen atoms, alkyl groups, hydroxyalkyl groups or alkoxyalkyl groups, and $R_4$ and $R_5$, which may be the same or different, represent hydrogen or halogen atoms, or trifluoromethyl groups or hydroxy groups or alkyl, alkoxy or alkylmercapto groups containing from 1 to 3 carbon atoms for use as analgesics, chemotherapeutic agents, antihistamines, and as antiphlogistic and antioedemic agents.

British Published Patent Application UK 1,177,956 discloses a process of preparing compounds of the formula:

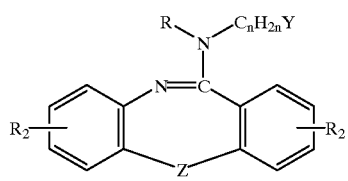

I wherein X is an oxygen or sulfur; one of $R_1$ and $R_2$ is hydrogen, $(C_1-C_6)$alkyl, $(C_1-C_6)$alkoxy, halogen or trifluoromethyl, and the other of $R_1$ and $R_2$ is hydrogen, $(C_1-C_6)$alkoxy or halogen; Y is hydroxy, amino, $(C_1-C_6)$ alkylamino, di-$(C_1-C_6)$alkylamino, 1-piperazinyl, 4-$(C_1-C_6)$-alkyl-1-piperazinyl, 4-hydroxy-$(C_1-C_6)$-alkyl-1-piperazinyl, pyrrolidino, $(C_1-C_6)$alkyl-pyrrolidino, piperidino, $(C_1-C_6)$alkyl piperidino, morpholino, or $(C_1-C_6)$alkylmorpholino; R is $(C_1-C_6)$alkyl; n is 2, 3, or 4; or the

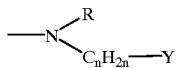

group taken together represents 1-piperazinyl, 4-$(C_1-C_6)$-alkyl-1-piperazinyl, or 4-hydroxy-$(C_1-C_6)$-alkyl-1-piperazinyl. These compounds were disclosed as having activity as tranquilizers and in some instances as antidepressants.

U.S. Pat. No. 3,539,573 discloses compounds of general Formula A:

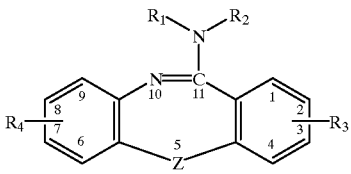

wherein Z denotes a member of the class consisting of bivalent sulfur, imino, and lower alkyl imino; $R_1$ is a member of the class consisting of hydrogen and alkyl with 1 to 5 carbon atoms, and $R_2$ is a member of the class consisting of hydrogen, alkyl having from 1 to 5 carbon atoms, phenyl, $R_5$-substituted phenyl, aminoalkyl having from 1 to 5 carbon atoms, lower alkylated aminoalkyl having from 2 to 8 carbon atoms, amino, and lower alkylated amino; or $R_1$ and $R_2$ together with N form a member of the class consisting of 1-pyrrolidinyl, piperidino, morpholino, thiomorpholino, 1-piperazinyl, 4-(lower alkyl)-1-piperazinyl, 4-(lower hydroxyalkyl)-1-piperazinyl, and 4-(lower alkoxy-lower alkyl)-1-piperazinyl; and $R_3$, $R_4$, and $R_5$ are members of the class consisting of hydrogen, halogen, hydroxy, trifluoromethyl, lower alkyl, lower alkoxy, and lower alkylthio; and (B) 11-basic substituted dibenzodiazepines and dibenzothiazepines having the general Formula B:

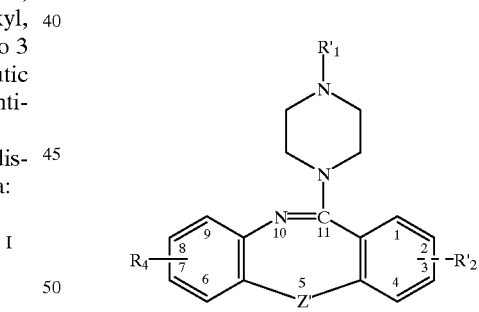

wherein Z' denotes a member of the group consisting of sulfur, sulphinyl, and imino; $R'_1$ represents a member of the group consisting of hydrogen, allyl, alkyl containing not more than 3 carbon atoms, hydroxyalkyl containing not more than 3 carbon atoms, alkoxyalkyl containing not more than 6 carbon atoms, and alkoyloxyalkyl containing not more than 6 carbon atoms; and $R'_2$ is a member of the group consisting of nitro, amino, aminosulphonyl of the formula —$SO_2NR'_3R'_4$ wherein $R'_3$ and $R'_4$ are the same or different members of the group consisting of hydrogen and methyl, alkylsulphinyl of the formula —$SOR'_5$ wherein $R'_5$ denotes alkyl with not more than 3 carbon atoms, and alkylsulphonyl of the formula —$SO_2R'_5$ wherein $R'_5$ denotes alkyl with not more than 3 carbon atoms; and (C) the nontoxic pharmaceutically acceptable acid-addition salts of (A) and (B).

These compounds are disclosed to be used as neuroplegics, neuroleptics, neuroleptic antidepressants, antiemetics, analgesics, sedatives, parasympathicolytics, and antihistaminics.

European Published Patent Application 0461869 discloses cysteine containing tetrapeptide inhibitors of PFT of the Formula Cys-Aaa$^1$-Aaa$^2$-Xaa.

European Published Patent Application 0520823 discloses cysteine containing tetrapeptide inhibitors of PFT of the Formula Cys-Xaa$^1$-dXaa$^2$-Xaa$^3$.

European Published Patent Application 0523873 discloses cysteine containing tetrapeptide inhibitors of PFT of the Formula Cys-Xaa$^1$-Xaa$^2$-Xaa$^3$.

European Published Patent Application 0528486 discloses cysteine containing tetrapeptide amides inhibitors of PFT of the Formula Cys-Xaa$^1$-Xaa$^2$-Xaa$^3$-NRR$^1$.

European Published Patent Application 0535730 discloses pseudotetrapeptide inhibitors of PFT of the following two formulas:

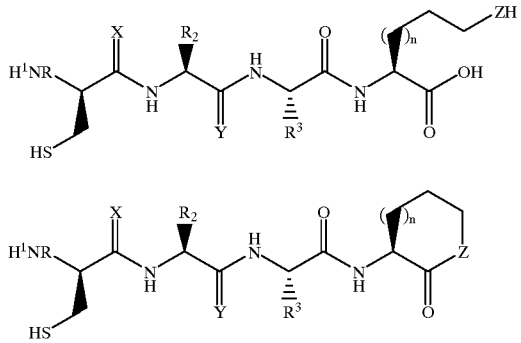

Copending U.S. patent application Ser. No. 08/268,364 discloses a series of histidine and homohistidine derivatives as inhibitors of protein farnesyltransferase.

Compounds disclosed in the above references do not disclose or suggest the novel combination of structural variations found in the present invention described hereinafter.

We have surprisingly and unexpectedly found that a series of tricyclic compounds are inhibitors of farnesyltransferase and thus useful as agents for the treatment of proliferative diseases such as, for example, cancer, restenosis, and psoriasis, and as antiviral agents.

SUMMARY OF THE INVENTION

Accordingly, the present invention is a compound of Formula I

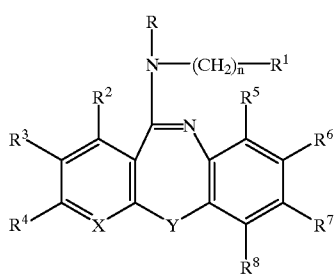

wherein X is C—R$^9$, wherein R$^9$ is as defined herein after or N;

Y is

wherein R$^{10}$ is hydrogen, alkyl, or substituted alkyl wherein the substituent on the alkyl group is selected from the group consisting of:

OR$^{11}$ wherein R$^{11}$ is hydrogen, or alkyl,

SR$^{11}$ wherein R$^{11}$ is as defined above,

CO$_2$R$^{12}$ wherein R$^{12}$ is hydrogen, alkyl, or benzyl,

wherein R$^{13}$ and R$^{14}$ are independently the same or different and each is hydrogen, alkyl, or R$^{13}$ and R$^{14}$ are taken together with N to form a 5- or 6-membered ring optionally containing a heteroatom selected from the group consisting of N, S, and O or

wherein R$^{13}$ and R$^{14}$ are as defined above, —CH$_2$—, —O—, —S(O)$_m$— wherein m is zero or an integer of 1 or 2,

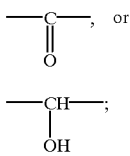

or

R is hydrogen, or alkyl;

n is an integer of 1 to 5;

R$^1$ is heteroaryl;

R$^2$, R$^3$, R$^4$, R$^5$, R$^6$, R$^7$, R$^8$, and R$^9$ are each independently the same or different and each is hydrogen, NO$_2$,

wherein R$^{13}$ and R$^{14}$ are as defined above,

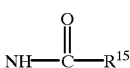

wherein R$^{15}$ is hydrogen, alkyl, or aryl,

CO$_2$R$^{12}$ wherein R$^{12}$ is as defined above,

wherein $R^{13}$ and $R^{14}$ are as defined above,

wherein $R^{16}$ is alkyl, aryl, or arylalkyl, halogen, CN, OH,
$SR^{17}$ wherein $R^{17}$ is hydrogen, or alkyl, SO alkyl, $SO_2$ alkyl, alkoxy, benzyloxy, alkyl, or substituted alkyl wherein the substituents on the alkyl group are as defined above;

with the proviso that at least two of $R^2$, $R^3$, $R^4$, or $R^9$ are hydrogen and at least one of $R^5$, $R^6$, $R^7$, or $R^8$ is hydrogen; and corresponding isomers thereof;

or a pharmaceutically acceptable salt thereof.

As inhibitors of farnesyltransferase, the compounds of Formula I are antiproliferative agents. Thus, they are useful for the treatment of cancer, restenosis, and psoriasis, and as antiviral agents. Additionally, a compound of Formula I may be combined with other conventional anti-cancer agents such as, for example, cisplatin.

A still further embodiment of the present invention is a pharmaceutical composition for administering an effective amount of a compound of Formula I in unit dosage form in the treatment methods mentioned above. Finally, the present invention is directed to methods for production of a compound of Formula I.

DETAILED DESCRIPTION OF THE INVENTION

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

"Alkoxy" and "thioalkoxy" are O-alkyl or S-alkyl of from 1 to 6 carbon atoms as defined above for "alkyl".

The term "aryl" means an aromatic radical which is a phenyl group, a naphthyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, N-acetylamino, cyano or nitro, or a naphthyl group substituted by 1 to 4 substituents as defined above for a phenyl group substituted by 1 to 4 substituents.

The term "heteroaryl" means a heteroaromatic radical which is 2- or 3-thienyl; 2- or 3-furanyl; 1-, 2- or 3-pyrrolyl; 1-, 2-, 4-, or 5-imidazolyl; 1-, 3-, 4-, or 5-pyrazolyl; 2-, 4-, or 5-thiazolyl; 3-, 4-, or 5-isothiazolyl; 2-, 4-, or 5-oxazolyl; 3-, 4-, or 5-isoxazolyl; 1-, 3-, or 5-1,2,4-triazolyl; 1-, 2-, 4-, or 5-1,2,3-triazolyl; 1- or 5-tetrazolyl; 4-, or 5-1,2,3-oxadiazolyl; 3-, or 5-1,2,4-oxadiazolyl; 2-1,3,4-oxadiazolyl; 2-1,3,4-thiadiazoyl; 2-1,3,5-triazinyl; 3-pyridinyl; 3-, 4-, or 5-pyridazinyl; 2-pyrazinyl; 2-, 4-, or 5-pyrimidinyl; unsubstituted or substituted by 1 to 2 substituents selected from $NH_2$, OH, SH, halogen as defined hereinafter, alkyl as defined above, or alkoxy as defined above.

The term "arylalkyl" means an aromatic radical attached to an alkyl radical wherein aryl and alkyl are as defined above for example benzyl, fluorenylmethyl, and the like.

"Halogen" is fluorine, chlorine, bromine, or iodine.

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharma. Sci.*, 66:1 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *J. of Pharma. Sci.*, 66:1 (1977)).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

A preferred compound of Formula I is one wherein $R^1$ is a heteroaryl radical selected from the group consisting of:
- 2- or 3-thienyl;
- 2- or 3-furanyl;
- 1-, 2- or 3-pyrrolyl;
- 1-, 2-, 4-, or 5-imidazolyl;
- 1-, 3-, 4-, or 5-pyrazolyl;
- 2-, 4-, or 5-thiazolyl;
- 3-, 4-, or 5-isothiazolyl;
- 2-, 4-, or 5-oxazolyl;
- 3-, 4-, or 5-isoxazolyl;
- 1-, 3-, or 5-1,2,4-triazolyl;
- 1-, 2-, 4- or 5-1,2,3-triazolyl;
- 1- or 5-tetrazolyl;
- 4- or 5-1,2,3-oxadiazolyl;
- 3- or 5-1,2,4-oxadiazolyl;
- 2-1,3,4-oxadiazolyl;
- 2-1,3,4-thiadiazoyl;
- 2-1,3,5-triazinyl;
- 3-pyridinyl;
- 3-, 4-, or 5-pyridazinyl;
- 2-pyrazinyl; and
- 2-, 4-, or 5-pyrimidinyl; or optionally, the heteroaryl radical is substituted with a substituent selected from the group consisting of:

$NH_2$, OH, SH, halogen, alkyl, or alkoxy.

A more preferred compound of Formula I is one wherein Y is —NH—

—O—, —S—, or —$SO_2$—;

n is an integer of 1 to 5;

$R^1$ is a heteroaryl radical selected from the group consisting of:
- 1-, 2-, or 4-imidazolyl, 3-pyridinyl, 1-, 3-, or 5-1,2,4-triazolyl, 5-thiazolyl, or 5-oxazolyl;

$R^3$ and $R^4$ are hydrogen or alkoxy;

$R^6$ and $R^7$ are hydrogen, halogen, mercaptomethyl, hydroxymethyl, alkoxy, alkyl, or benzyloxy.

Particularly valuable is a compound selected from the group consisting of:
- (8-Chloro-5H-dibenzo[b,e][1,4]diazepin-11-yl)pyridin-3-ylmethyl-amine;
- (8-Chloro-5H-dibenzo[b,e][1,4]diazepin-11-yl)-[2-(3H-imidazol-4-yl)-ethyl]-amine;
- (8-Chloro-5H-dibenzo[b,e][1,4]diazepin-11-yl)-(2-pyridin-3-yl-ethyl)-amine;
- (8-Chloro-5H-dibenzo[b,e][1,4]diazepin-11-yl)-(2-imidazol-1-yl-ethyl)-amine;
- (8-Chloro-5H-dibenzo[b,e][1,4]diazepin-11-yl)-(3-imidazol-1-yl-propyl)-amine;
- (7-Chloro-5H-dibenzo[b,e][1,4]diazepin-11-yl)pyridin-3-ylmethyl-amine;
- (5H-Dibenzo[b,e][1,4]diazepin-11-yl)-pyridin-3-ylmethyl-amine;
- (8-Methyl-5H-dibenzo[b,e][1,4]diazepin-11-yl)pyridin-3-ylmethyl-amine;
- (8-Methoxy-5H-dibenzo[b,e][1,4]diazepin-11-yl)pyridin-3-ylmethyl-amine;
- (8-Bromo-5H-dibenzo[b,e][1,4]diazepin-11-yl)pyridin-3-ylmethyl-amine;
- (7,8-Dichloro-5H-dibenzo[b,e][1,4]diazepin-11-yl)pyridin-3-ylmethyl-amine;
- (8-Benzyloxy-5H-dibenzo[b,e][1,4]diazepin-11-yl)pyridin-3-ylmethyl-amine;
- (7,8-Dichloro-2,3-dimethoxy-5H-dibenzo[b,e][1,4]diazepin-11-yl)-pyridin-3-ylmethyl-amine;
- (11H-Benzo[b]pyrido[2,3-e][1,4]diazepin-5-yl)pyridin-3-ylmethyl-amine;
- (8-Chloro-5-methyl-5H-dibenzo[b,e][1,4]diazepin-11-yl)-pyridin-3-ylmethyl-amine;
- (8-Chloro-dibenzo[b,f][1,4]thiazepin-11-yl)pyridin-3-ylmethyl-amine;
- (8-Chloro-5,5-dioxo-5H-5$\lambda^6$-dibenzo[b,f][1,4]thiazepin-11-yl)-pyridin-3-ylmethyl-amine; and
- (8-Chloro-dibenzo[b,f][1,4]oxazepin-11-yl)pyridin-3-ylmethyl-amine; and corresponding isomers thereof; or a pharmaceutically acceptable salt thereof.

The compounds of Formula I are valuable inhibitors of the enzyme farnesyltransferase.

The protein:farnesyltransferase (PFT) or farnesyl protein transferase (FPT) inhibitory activity of compounds of Formula I was assayed in HEPES buffer (pH 7.4) containing 5 mM potassium phosphate and 20 $\mu$M $ZnCl_2$. The solution also contained 7 mM DTT, 1.2 mM $MgCl_2$, 0.1 mM leupeptin, 0.1 mM pepstatin, and 0.2 mM phenylmethylsulfonyl fluoride. Assays were performed in 96 well plates (Wallec) and employed solutions composed of varying concentrations of a compound of Formula I in 100% DMSO. Upon addition of both substrates, radiolabeled farnesyl pyrophosphate ([1-$^3$H], specific activity 15–30 Ci/mmol, final concentration 0.12 $\mu$M) and (biotinyl)-Ahe-Tyr-Lys-Cys-Val-Ile-Met peptide (final concentration 0.2 $\mu$M), the enzyme reaction was started by addition of 40-fold purified rat brain farnesyl protein transferase. After incubation at 37° for 30 minutes, the reaction was terminated by diluting the reaction 2.5-fold with a stop buffer containing 1.5M magnesium acetate, 0.2M $H_3PO_4$, 0.5% BSA, and strepavidin beads (Amersham) at a concentration of 1.3 mg/mL. After allowing the plate to settle for 30 minutes at room temperature, radioactivity was quantitated on a microBeta counter (Model 1450, Wallec). Compounds of Formula I show $IC_{50}$ values of 0.8 to 60 $\mu$M in this assay and are thus valuable inhibitors of protein:farnesyltransferase enzyme which may be used in the medical treatment of tissue proliferative diseases, including cancer and restenosis. The assay was also carried out without 5 mM potassium phosphate.

Gel Shift Assay

Twenty-four hours after planting 2×10$^6$ ras-transformed cells per treatment condition, the farnesylation inhibitor is added at varying concentrations. Following an 18-hour incubation period, cells are lysed in phosphate-buffered saline containing 1% Triton X-100, 0.5% sodium deoxycholate, and 0.1% SDS, pH 7.4 in the presence of several protease inhibitors (PMSF, antipain, leupeptin, pepstatin A, and aprotinin all at 1 $\mu$g/mL). Ras protein is immunoprecipitated from the supernatants by the addition of 3 $\mu$g v-H-ras Ab-2 (Y13-259 antibody from oncogene Science). After overnight immunoprecipitation, 30 $\mu$L of a 50% protein G-Sepharose slurry (Pharmacia) is added followed by 45-minute incubation. Pellets are resuspended in 2× tris-glycine loading buffer (Novex) containing 5% B-mercaptoethanol and then denatured by 5 minutes boiling prior to electrophoresis on 14% Tris-glycine SDS gels. Using Western transfer techniques, proteins are transferred to nitrocellulose membranes followed by blocking in blocking buffer. Upon overnight incubation with primary antibody (pan-ras Ab-2 from Oncogene Science), an antimouse HRP conjugate secondary antibody (Amersham) is employed for detection of the ras protein. Blots are developed using ECL techniques (Amersham).

Antiproliferation Assay

H-Ras-transformed cells (total of $1 \times 10^5$ cells per treatment condition) are planted into T-25 flasks. Forty-eight hours later, the farnesylation inhibitor is, added at varying concentrations. After 72-hour exposure, cells are trypsinized and viability quantitated by counting the number of trypan blue-excluding cells on a hemacytometer.

The data in Table 1 show farnesyl protein transferase inhibitory activity, activity in the gel shift assay against ras protein, and inhibition of cell growth of selected compounds of Formula I.

TABLE 1

Biological Activity of Compounds of Formula I

| Example | Compound | Farnesyl Protein Transferase Inhibition | | Gel Shift | Cell Growth Inhibition |
|---|---|---|---|---|---|
| | | Hepes IC$_{50}$ ($\mu$M) | Hepes/ 5 mM PO$_4^{-3}$ IC$_{50}$ ($\mu$M) | Minimum Effective Dose ($\mu$M) | H-Ras-transformed Cells |
| 1 | (8-Chloro-5H-dibenzo [b,e][1,4]diazepin-11-yl)pyridin-3-ylmethyl-amine | 3.7 | 5.0 | 50 | 11 |
| 2 | (8-Chloro-5H-dibenzo [b,e][1,4]-diazepin-11-yl)-[2-(3H-imidazol-4-yl)-ethyl]-amine | 2.4 | 3.0 | 25 | 4 |
| 3 | (8-Chloro-5H-dibenzo [b,e][1,4]diazepin-11-yl)-(2-pyridin-3-yl-ethyl)-amine | 36 | 57 | >50 | 13 |
| 4 | (8-Chloro-5H-dibenzo [b,e][1,4]diazepin-11-yl)-(2-imidazol-1-yl-ethyl)-amine | 3.0 | 2.5 | 5 | — |
| 5 | (8-Chloro-5H-dibenzo b,e][1,4]diazepin-11-yl)-(3-imidazol-1-yl-propyl)-amine | 6.8 | 4.5 | 2.5 | — |
| 6 | (7-Chloro-5H-dibenzo [b,e]-[1,4]diazepin-11-yl)pyridin-3-ylmethyl-amine | 5.5 | 5.6 | 50 | — |
| 7 | (5H-Dibenzo[b,e][1,4] diazepin-11-yl)-pyridin-3-ylmethyl-amine | 23 | 12 | 50 | >50 |
| 8 | (8-Methyl-5H-dibenzo [b,e][1,4]diazepin-11-yl)-pyridin-3-ylmethyl-amine | 24 | 31 | — | 7 |
| 9 | (8-Methoxy-5H-dibenzo [b,e][1,4]diazepin-11-yl)-pyridin-3-ylmethyl-amine | 27 | 16 | 50 | >50 |
| 10 | (8-Bromo-5H-dibenzo[b,e] [1,4 ]diazepin-11-yl)-pyridin-3-ylmethyl-amine | 6 | 36 | | |
| 11 | (7,8-Dichloro-5H-dibenzo [b,e][1,4]diazepin-11-yl)-pyridin-3-ylmethyl-amine | 0.8 | 1.6 | 50 | 18 |
| 12 | (8-Benzyloxy-5H-dibenzo [b,e][1,4]diazepin-11-yl)-pyridin-3-ylmethyl-amine | >50 | 37 | >50 | 7 |
| 13 | (7,8-Dichloro-2,3-dimethoxy-5H-dibenzo [b,e][1,4]diazepin-11-yl)-pyridin-3-ylmethyl-amine | 30 | 50 | — | — |
| 14 | (11H-Benzo[b]pyrido [2,3-e][1,4]diazepin-5-yl)-pyridin-3-ylmethyl-amine | 14 | 17 | 50 | >50 |
| 15 | (8-Chloro-5-methyl-5H-dibenzo[b,e][1,4]- | 12.2 | 17 | >25 | — |

TABLE 1-continued

Biological Activity of Compounds of Formula I

| Example | Compound | Farnesyl Protein Transferase Inhibition | | Gel Shift | Cell Growth Inhibition |
|---|---|---|---|---|---|
| | | Hepes IC$_{50}$ ($\mu$M) | Hepes/ 5 mM PO$_4^{-3}$ IC$_{50}$ ($\mu$M) | Minimum Effective Dose ($\mu$M) | H-Ras-transformed Cells |
| | diazepin-11-yl)-pyridin-3-ylmethyl-amine | | | | |
| 16 | (8-Chloro-dibenzo[b,f][1,4]thiazepin-11-yl)-pyridin-3-ylmethyl-amine | 9.8 | 22 | — | — |
| 17 | (8-Chloro-5,5-dioxo-5H-5$\lambda^6$-dibenzo[b,f][1,4]-thiazepin-11-yl)-pyridin-3-ylmethyl-amine | 5.0 | 6.1 | — | — |
| 18 | (8-Chloro-dibenzo[b,f][1,4]oxazepin-11-yl)-pyridin-3-ylmethyl-amine | 8.7 | 16.5 | — | — |

A compound of Formula Ia

Ia wherein X is C—$R^9$ wherein $R^9$ is as defined hereinafter or N;

R is hydrogen, or alkyl;

n is an integer of 1 to 5;

$R^1$ is heteroaryl;

$R^2$, $R^3$, $R^4$, $R^5$, $R^6$, $R^7$, $R^8$, and $R^9$ are each independently the same or different and each is hydrogen, $NO_2$, $$\underset{R^{14}}{\overset{}{N}}{-}R^{13}$$

wherein $R^{13}$ and $R^{14}$ are independently the same or different and each is hydrogen, alkyl, or $R^{13}$ and $R^{14}$ are taken together with N to form a 5- or 6-membered ring optionally containing a heteroatom selected from the group consisting of N, S, and O, $$NH{-}\overset{O}{\underset{}{C}}{-}R^{15}$$

wherein $R^{15}$ is hydrogen, alkyl, or aryl, $CO_2R^{12}$ wherein $R^{12}$ is hydrogen, alkyl, or aryl, $$\underset{R^{14}}{\overset{}{CON}}R^{13}$$

wherein $R^{13}$ and $R^{14}$ are as defined above, $$-\overset{O}{\underset{}{C}}-R^{16}$$

wherein $R^{16}$ is alkyl, aryl, or arylalkyl, halogen, CN, OH, $SR^{17}$ wherein $R^{17}$ is hydrogen, or alkyl, SO alkyl, $SO_2$ alkyl, alkoxy, benzyloxy, alkyl, or substituted alkyl wherein the substituent on the alkyl group is selected from the group consisting of:

$OR^{11}$ wherein $R^{11}$ is hydrogen, or alkyl, $SR^{11}$ wherein $R^{11}$ is as defined above, $CO_2R^{12}$ wherein $R^{12}$ is hydrogen, alkyl, or benzyl, $$\underset{R^{14}}{\overset{}{CON}}R^{13}$$

wherein $R^{13}$ and $R^{14}$ are as defined above or, $$\underset{R^{14}}{\overset{}{N}}{-}R^{13}$$

wherein $R^{13}$ and $R^{14}$ are as defined above;

with the proviso that at least two of $R^2$, $R^3$, $R^4$, or $R^9$ are hydrogen and at least one of $R^5$, $R^6$, $R^7$, or $R^8$ is hydrogen;

and corresponding isomers thereof;

or a pharmaceutically acceptable salt thereof may be prepared by reaction of a compound of Formula II

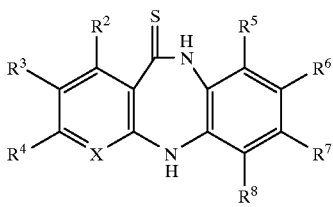

II wherein X, $R^2$, $R^3$, $R^4$, $R^5$, $R^6$, $R^7$, and $R^8$ are as defined above with a compound of Formula III

III wherein n and $R^1$ are as defined above in a solvent such as, for example, 2-ethoxyethanol and the like at about room temperature to about the reflux temperature of the solvent for about 4 hours to about 30 hours to afford a compound of Formula Ia. Preferably, the reaction is carried out in 2-ethoxyethanol at about reflux for about 30 hours.

A compound of Formula II may be prepared from a compound of Formula IV

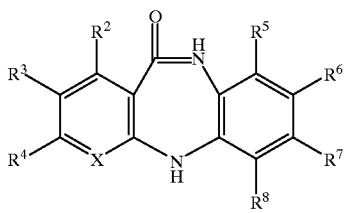

IV wherein X, $R^2$, $R^3$, $R^4$, $R^5$, $R^6$, $R^7$, and $R^8$ are as defined above by reaction with Lawesson's Reagent, [2,4-bis(4-methoxyphenyl)-1,3-dithia-2,4-diphosphetane-2,4-disulfide], in a solvent such as, for example, pyridine and the like to afford a compound of Formula II.

A compound of Formula IV may be prepared from a compound of Formula V

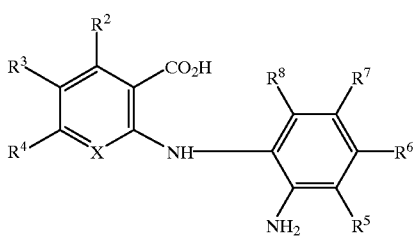

V wherein X, $R^2$, $R^3$, $R^4$, $R^5$, $R^6$, $R^7$, and $R^8$ are as defined above by reaction with diphenylphosphoryl azide in a solvent such as, for example, dimethylformamide and the like and a base such as, for example, triethylamine and the like at about room temperature for about 1 hour to about 24 hours to afford a compound of Formula IV. Preferably, the reaction is carried out in dimethylformamide and triethylamine at about room temperature for about 24 hours. Alternatively, the reaction may be carried out with N,N'-dicyclohexylcarbodiimide in a solvent such as, for example, dimethylformamide and the like at about room temperature for about 24 hours to afford a compound of Formula IV.

A compound of Formula V may be prepared from a compound of Formula VI

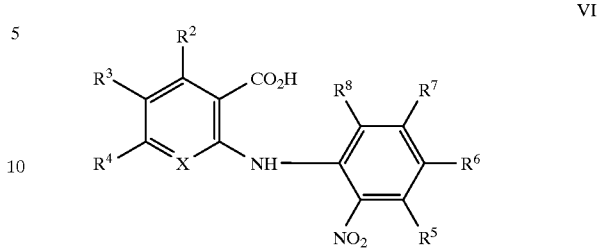

VI wherein X, $R^2$, $R^3$, $R^4$, $R^5$, $R^6$, $R^7$, and $R^8$ are as defined above by reaction with hydrogen in the presence of a catalyst such as, for example, Raney nickel and the like in a solvent such as, for example, tetrahydrofuran and the like at about room temperature and a pressure of about 50 pounds per square inch (psi) to afford a compound of Formula V. Preferably, the reaction is carried out with Raney nickel in tetrahydrofuran at about 50 psi.

A compound of Formula VI may be prepared by reaction of a compound of Formula VII

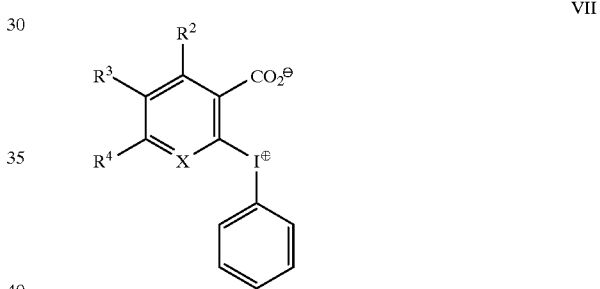

VII wherein X, $R^2$, $R^3$, and $R^4$ are as defined above with a compound of Formula VIII

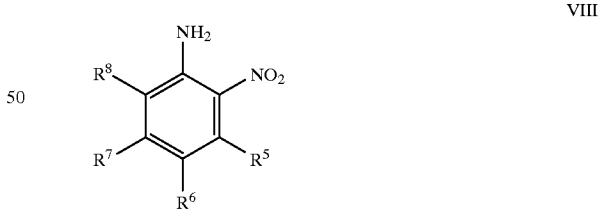

VIII wherein $R^5$, $R^6$, $R^7$, and $R^8$ are as defined above in the presence of copper (II) acetate in a solvent such as, for example, isopropanol and the like at about room temperature to about reflux temperature for about 1 hour to about 24 hours to afford a compound of Formula VI. Preferably, the reaction is carried out in isopropanol at reflux for about 24 hours.

Alternatively, a compound of Formula Ia may be prepared by reaction of a compound of Formula IX

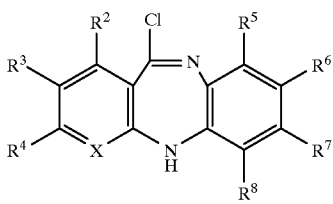

wherein X, $R^2$, $R^3$, $R^4$, $R^5$, $R^6$, $R^7$, and $R^8$ are as defined above with a compound of Formula III using conventional methodology to afford a compound of Formula Ia.

A compound of Formula IX may be prepared from a compound of Formula IV in the presence of phosphorus oxychloride using conventional methodology to afford a compound of Formula IX.

Alternatively, a compound of Formula Ia may be prepared by reaction of a compound of Formula X

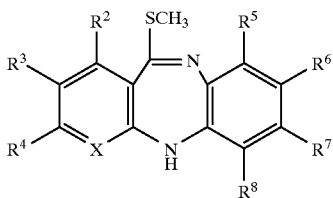

wherein X, $R^2$, $R^3$, $R^4$, $R^5$, $R^6$, $R^7$, and $R^8$ are as defined above using conventional methodology to afford a compound of Formula Ia.

A compound of Formula X may be prepared from a compound of Formula II and methyl iodide using conventional methodology to afford a compound of Formula X.

A compound of Formula Ib

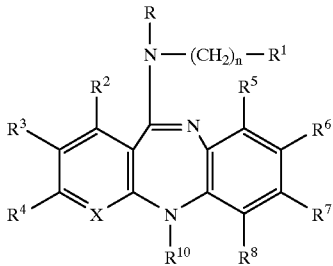

wherein $R^{10}$ is hydrogen, alkyl, or substituted alkyl wherein the substituent on the alkyl group is selected from the group consisting of:

$OR^{11}$ wherein $R^{11}$ is hydrogen, or alkyl, $SR^{11}$ wherein $R^{11}$ is as defined above, $CO_2R^{12}$ wherein $R^{12}$ is hydrogen, alkyl, or benzyl,

wherein $R^{13}$ and $R^{14}$ are independently the same or different and each is hydrogen, alkyl, or $R^{13}$ and $R^{14}$ are taken together with N to form a 5- or 6-membered ring optionally containing a heteroatom selected from the group consisting of N, S, and O or

wherein $R^{13}$ and $R^{14}$ are as defined above, and X, n, R, $R^1$, $R^2$, $R^3$, $R^4$, $R^5$, $R^6$, $R^7$, and $R^8$ are as defined above may be prepared by reaction of a compound of Formula XI

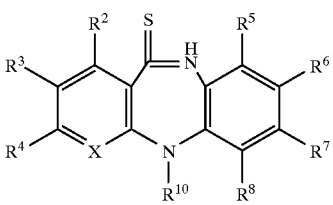

wherein X, $R^2$, $R^3$, $R^4$, $R^5$, $R^6$, $R^7$, $R^8$, and $R^{10}$ are as defined above with a compound of Formula III using methodology previously described for preparing a compound of Formula Ia from a compound of Formula II and a compound of Formula III to afford a compound of Formula Ib.

A compound of Formula XI is prepared from a compound of Formula XII

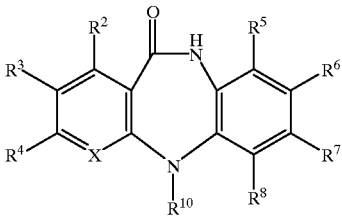

wherein X, $R^2$, $R^3$, $R^4$, $R^5$, $R^6$, $R^7$, $R^8$, and $R^{10}$ are as defined above using methodology previously described for preparing a compound of Formula II from a compound of Formula IV to afford a compound of Formula XI, with the proviso that $R^{10}$ cannot contain an amide group when a compound of Formula XII is converted to a compound of Formula XI. To prepare a compound of Formula XI with $R^{10}$ containing an amide group, a compound of Formula XII is prepared with $R^{10}$ containing an ester group, for example, an alkyl ester. After converting a compound of Formula XII to a compound of Formula XI with $R^{10}$ containing an ester group, the ester group is hydrolyzed to the corresponding acid with a base such as, for example, dilute sodium hydroxide and the like and the corresponding acid converted to the desired amide using conventional mixed anhydride methodology or carbodiimide methodology.

A compound of Formula XII is prepared from a compound of Formula XIII

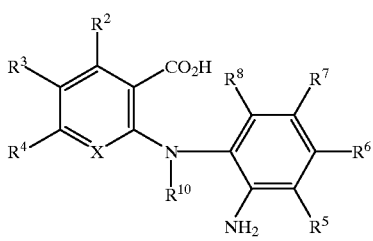

XIII wherein X, $R^2$, $R^3$, $R^4$, $R^5$, $R^6$, $R^7$, $R^8$, and $R^{10}$ are as defined above using methodology previously described for preparing a compound of Formula IV from a compound of Formula V to afford a compound of Formula XII, with the proviso that $R^{10}$ cannot contain an amide group when a compound of Formula XIII is converted to a compound of Formula XII. To prepare a compound of Formula XII with $R^{10}$ containing an amide group, one must use the methodology previously described for preparing a compound of Formula XI wherein $R^{10}$ contains an amide group.

A compound of Formula XIII is prepared from a compound of Formula XIV

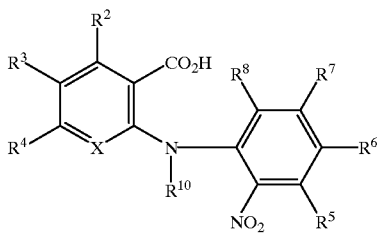

XIV wherein X, $R^2$, $R^3$, $R^4$, $R^5$, $R^6$, $R^7$, $R^8$, and $R^{10}$ are as defined above using methodology previously described for preparing a compound of Formula V from a compound of Formula VI to afford a compound of Formula XIII.

A compound of Formula XIV is prepared from a compound of Formula XV

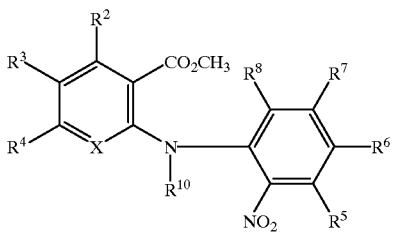

XV wherein X, $R^2$, $R^3$, $R^4$, $R^5$, $R^6$, $R^7$, $R^8$, and $R^{10}$ are as defined above by hydrolysis using a base such as, for example, sodium hydroxide and the like in a solvent such as, for example, methanol and the like to afford a compound of Formula XIV. Preferably, the reaction is carried out with sodium hydroxide in methanol. When $R^{10}$ contains an ester group, it is necessary to distinguish this ester from the aromatic ester undergoing hydrolysis on the ring. In this event, the $R^{10}$ ester group is preferably a tertiary butyl ester. After hydrolyzing a compound of Formula XV with $R^{10}$ containing a tertiary butyl ester to a compound of Formula XIV, a compound of Formula XIV is converted to a compound of Formula XIII, and then cyclized to a compound of Formula XII and converted to the thioamide of Formula XI. The tertiary butyl ester in $R^{10}$ is then hydrolyzed with an acid such as, for example, trifluoroacetic acid and the like to the corresponding acid and the acid converted to the desired ester with the BOP reagent (benzotriazol-1-yloxytris (dimethylamino)phosphonium hexafluorophosphate) and the corresponding alcohol in a solvent such as, for example, dimethylformamide and the like.

A compound of Formula XV is prepared from a compound of Formula XVI

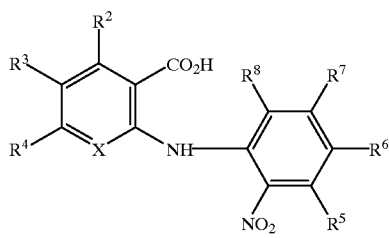

XVI wherein X, $R^2$, $R^3$, $R^4$, $R^5$, $R^6$, $R^7$, and $R^8$ are as defined above and a compound of Formula XVII $R^{10}I$  XVII wherein $R^{10}$ is as defined above in the presence of a base such as, for example, sodium hydride and the like in a solvent such as, for example, dimethylformamide and the like to afford a compound of Formula XV.

A compound of Formula Ic

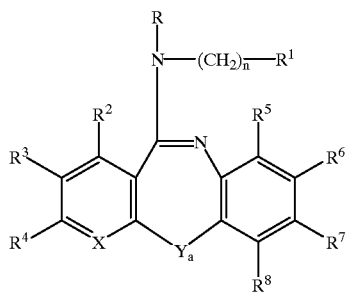

Ic wherein $Y_a$ is —O— or —S— and X, n, R, $R^1$, $R^2$, $R^3$, $R^4$, $R^5$, $R^6$, $R^7$, and $R^8$ are as defined above is prepared from a compound of Formula XVIII

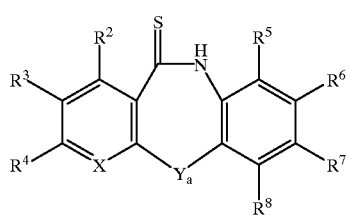

XVIII wherein X, $Y_a$, $R^2$, $R^3$, $R^4$, $R^5$, $R^6$, $R^7$, and $R^8$ are as defined above using methodology previously described for preparing a compound of Formula Ia from a compound of Formula II and a compound of Formula III to afford a compound of Formula Ic.

A compound of Formula XVIII is prepared from a compound of Formula XIX

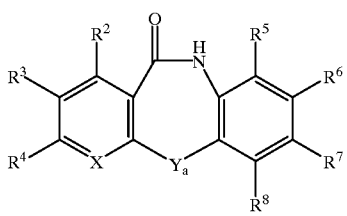

XIX wherein X, $Y_a$, $R^2$, $R^3$, $R^4$, $R^5$, $R^6$, $R^7$, and $R^8$ are as defined above using methodology previously described for preparing a compound of Formula II from a compound of Formula IV to afford a compound of Formula XVIII.

A compound of Formula XIX is prepared from a compound of Formula XX

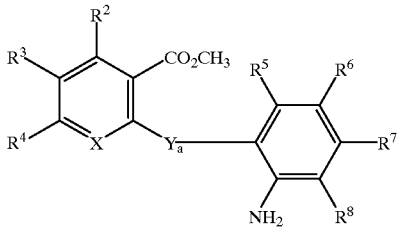

XX wherein X, $Y_a$, $R^2$, $R^3$, $R^4$, $R^5$, $R^6$, $R^7$, and $R^8$ are as defined above by heating at about 225° C. to afford a compound of Formula XIX.

A compound of Formula XX is prepared from a compound of Formula XXI

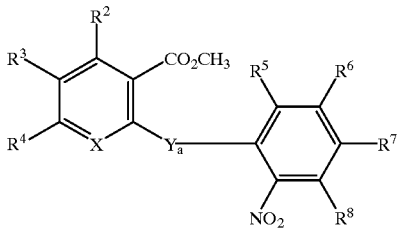

XXI wherein X, $Y_a$, $R^2$, $R^3$, $R^4$, $R^5$, $R^6$, $R^7$, and $R^8$ are as defined above using methodology previously described for preparing a compound of Formula V from a compound of Formula VI to afford a compound of Formula XX.

A compound of Formula XXI is prepared from a compound of Formula XXII

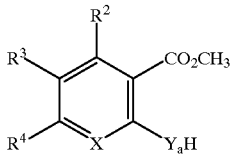

XXII wherein X, $Y_a$, $R^2$, $R^3$, and $R^4$ are as defined above and a compound of Formula XXIII

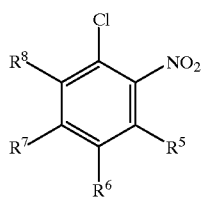

XXIII wherein $R^5$, $R^6$, $R^7$, and $R^8$ are as defined above in the presence of a base such as, for example, sodium hydride and the like in a solvent such as, for example, dimethylformamide and the like to afford a compound of Formula XXI.

A compound of Formula Id

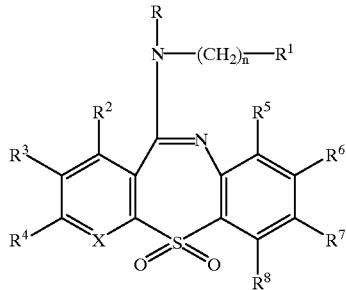

Id wherein X, n, R, $R^1$, $R^2$, $R^3$, $R^4$, $R^5$, $R^6$, $R^7$, and $R^8$ are as defined above is prepared from a compound of Formula XXIV

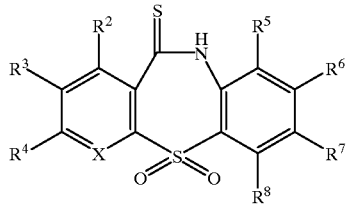

XXIV wherein X, $R^2$, $R^3$, $R^4$, $R^5$, $R^6$, $R^7$, and $R^8$ as defined above using methodology previously described for preparing a compound of Formula Ia from a compound of Formula II and a compound of Formula III to afford a compound of Formula Id.

A compound of Formula XXIV is prepared from a compound of Formula XXV

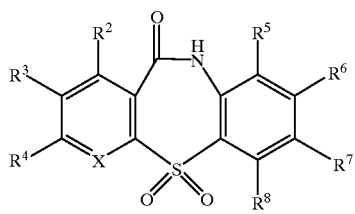

XXV wherein X, $R^2$, $R^3$, $R^4$, $R^5$, $R^6$, $R^7$, and $R^8$ are as defined above using methodology previously described for preparing a compound of Formula II from a compound of Formula IV to afford a compound of Formula XXIV.

A compound of Formula XXV is prepared from a compound of Formula XXVI

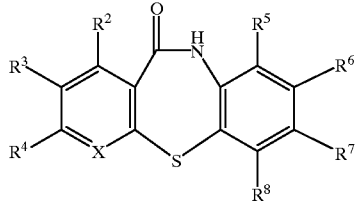

XXVI wherein X, $R^2$, $R^3$, $R^4$, $R^5$, $R^6$, $R^7$, and $R^8$ are as defined above by reaction with an oxidizing agent such as, for example, hydrogen peroxide and the like in a solvent such as, for example, acetic acid and the like to afford a compound of Formula XXV.

A compound of Formula Ie

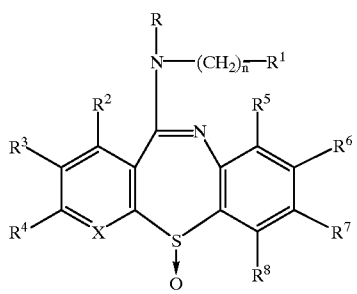

Ie wherein X, n, R, $R^1$, $R^2$, $R^3$, $R^4$, $R^5$, $R^6$, $R^7$, and $R^8$ are as defined above is prepared from a compound of Formula XXVII

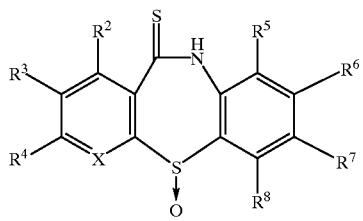

XXVII wherein X, $R^2$, $R^3$, $R^4$, $R^5$, $R^6$, $R^7$, and $R^8$ are as defined above using methodology previously described for preparing a compound of Formula Ia from a compound of Formula II and a compound of Formula III to afford a compound of Formula Ie.

A compound of Formula XXVII is prepared from a compound of Formula XXVIII

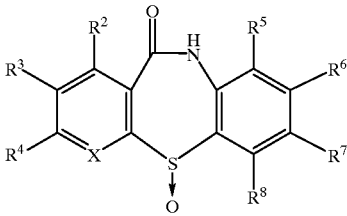

XXVIII wherein X, $R^2$, $R^3$, $R^4$, $R^5$, $R^6$, $R^7$, and $R^8$ are as defined above using methodology previously described for preparing a compound of Formula II from a compound of Formula IV to afford a compound of Formula XXVII.

A compound of Formula XXVIII is prepared from a compound of Formula XXVI by reaction with an oxidizing agent such as, for example, iodobenzene diacetate and the like in a solvent such as, for example, dimethylformamide and the like to afford a compound of Formula XXVIII.

A compound of Formula If

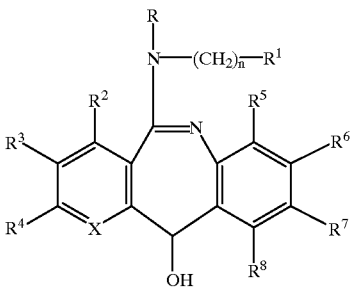

If wherein X, n, R, $R^1$, $R^2$, $R^3$, $R^4$, $R^5$, $R^6$, $R^7$, and $R^8$ are as defined is prepared from a compound of Formula Ig

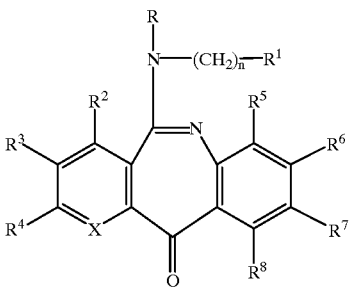

Ig wherein X, n, R, $R^1$, $R^2$, $R^3$, $R^4$, $R^5$, $R^6$, $R^7$, and $R^8$ are above by reaction with a metal hydride such as, for example, sodium borohydride and the like in a solvent such as, for example, methanol and the like to afford a compound of Formula If.

A compound of Formula Ig is prepared from a compound of Formula XXIX

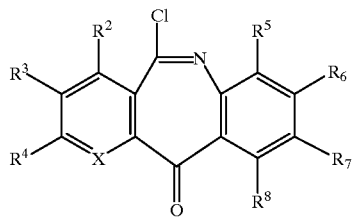

XXIX wherein X, $R^2$, $R^3$, $R^4$, $R^5$, $R^6$, $R^7$, and $R^8$ are as defined above by reaction of the iminochloride of Formula XXIX in ethyleneglycol, diethyl ether in the presence of two equivalents of a compound of Formula III to afford a compound of Formula Ig.

A compound of Formula XXIX is prepared from a compound of Formula XXX

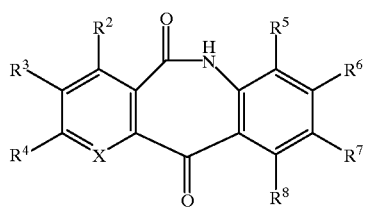

XXX wherein X, $R^2$, $R^3$, $R^4$, $R^5$, $R^6$, $R^7$, and $R^8$ are as defined above by reacting a compound of Formula XXX with phosphorus oxychloride in the presence of N,N,-dimethylaniline to afford a compound of Formula XXIX.

A compound of Formula XXX is prepared from a compound of Formula XXXI

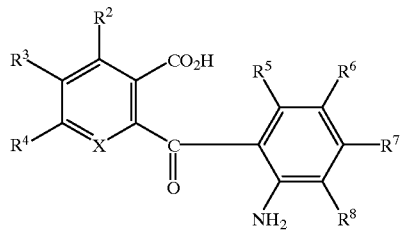

XXXI wherein X, $R^2$, $R^3$, $R^4$, $R^5$, $R^6$, $R^7$, and $R^8$ are as defined above using methodology previously described for preparing a compound of Formula XIX from a compound of Formula XX to afford a compound of Formula XXX.

A compound of Formula XXXI is prepared from a compound of Formula XXXII

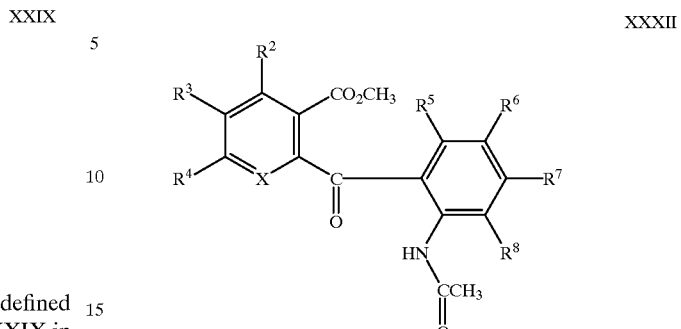

XXXII wherein X, $R^2$, $R^3$, $R^4$, $R^5$, $R^6$, $R^7$, and $R^8$ are as defined above using methodology previously described for preparing a compound of Formula XIV from a compound of Formula XV to afford a compound of Formula XXXI.

A compound of Formula XXXII is prepared from a compound of Formula XXXIII

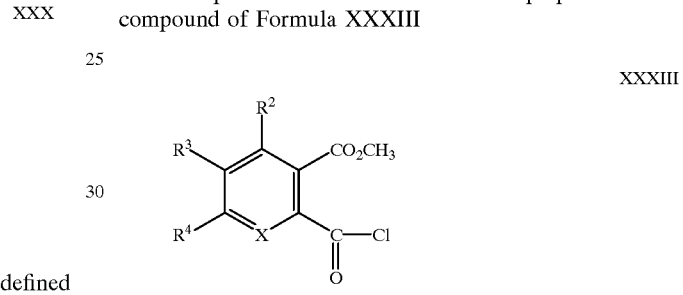

XXXIII wherein X, $R^2$, $R^3$, and $R^4$ are as defined above and a compound of Formula XXXIV

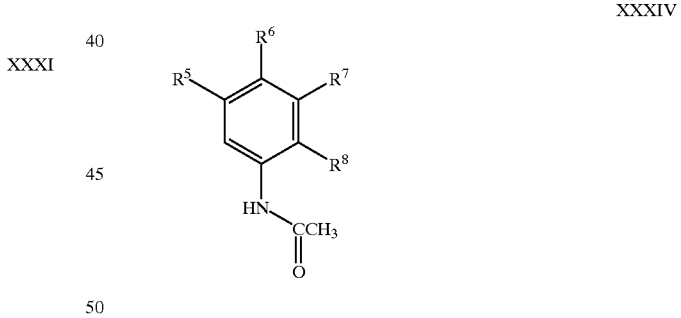

XXXIV wherein $R^5$, $R^6$, $R^7$, and $R^8$ are as defined above in the presence of a Lewis acid such as, for example, aluminum chloride and the like in a solvent such as, for example, tetrachloroethane and the like to afford a compound of Formula XXXII.

A compound of Formula Ih

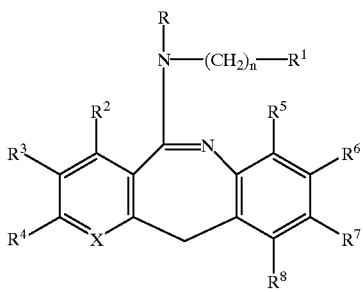

wherein X, n, R, $R^1$, $R^2$, $R^3$, $R^4$, $R^5$, $R^6$, $R^7$, and $R^8$ are as defined above is prepared from a compound of Formula XXXV

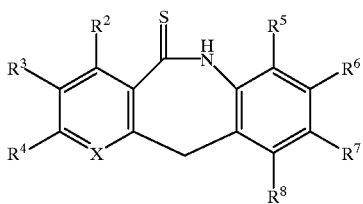

wherein X, $R^2$, $R^3$, $R^4$, $R^5$, $R^6$, $R^7$, and $R^8$ are as defined above using methodology previously described for preparing a compound of Formula Ia from a compound of Formula II and a compound of Formula III to afford a compound of Formula Ih.

A compound of Formula XXXV is prepared from a compound of Formula XXXVI

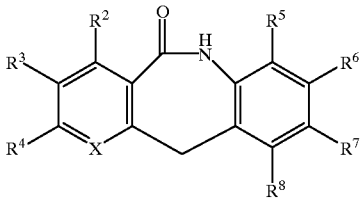

wherein X, $R^2$, $R^3$, $R^4$, $R^5$, $R^6$, $R^7$, and $R^8$ are as defined above using methodology previously described for preparing a compound of Formula II from a compound of Formula IV to afford a compound of Formula XXXV.

A compound of Formula XXXVI is prepared from a compound of Formula XXXVII

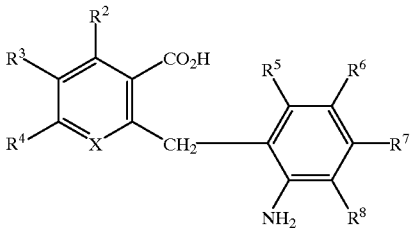

wherein X, $R^2$, $R^3$, $R^4$, $R^5$, $R^6$, $R^7$, and $R^8$ are as defined above using N,N'-dicyclohexylcarbodiimide in a solvent such as, for example, dimethylformamide and the like at about room temperature for about 24 hours to afford a compound of Formula XXXVI.

A compound of Formula XXXVII is prepared from a compound of Formula XXXI by reaction with hydrazine in the presence of a base such as, for example, potassium hydroxide and the like in a solvent such as, for example, ethyleneglycol and the like to afford a compound of Formula XXXVII.

Compounds of Formula III, Formula VII, Formula VIII, Formula XVI, Formula XVII, Formula XXII, Formula XXIII, Formula XXXIII, and Formula XXXIV are either known or capable of being prepared by methods known in the art.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as anticancer agents and as agents to treat restenosis and psoriasis, and as antiviral agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

(8-Chloro-5H-dibenzo[b,e][1,4]diazepin-11-yl) pyridin-3-ylmethyl-amine

A solution of 0.39 g (1.5 mmol) of 8-chloro-5,10-dihydro-dibenzo[b,e][1,4]diazepin-11-thione (Hunziker F., et al., *Helv. Chim. Acta,* 50:1588 (1967)) in 10 mL of 2-ethoxyethanol was treated with 0.3 mL (2.99 mmol) of 3-(aminomethyl)pyridine and heated at reflux for 30 hours. The solvent was removed under reduced pressure and the residue mixed with EtOAc and filtered to give 200 mg of the product. The filtrate was chromatographed on silica gel, eluting with EtOAc to give an additional 200 mg of product. Total yield 400 mg (80% yield) of the product as a yellow solid, mp 230–234° C. The structure was confirmed by NMR and mass spectroscopy. (m+H)$^+$=335.

EXAMPLE 2

(8-Chloro-5H-dibenzo[b,e][1,4]diazepin-11-yl)-[2-(3H-imidazol-4-yl)-ethyl]-amine A solution of 5.8 g (0.022 mol) of 8-chloro-5,10-dihydro-dibenzo[b,e][1,4]diazepin-11-thione in 145 mL of 2-ethoxyethanol was treated with 4.94 g (0.044 mol) of histamine and heated at reflux overnight. The solvent was removed under reduced pressure and the residue taken up in EtOAc and washed three times with H$_2$O, then saturated NaHCO$_3$ solution, then saturated NaCl solution. Drying over MgSO$_4$ and removal of the solvent under reduced pressure left the crude product as a yellow foam. This was dissolved in CH$_2$Cl$_2$ and slowly treated with hexane to give 7.44 g (99.2% yield) of the product as an amorphous yellow solid. The structure was confirmed by NMR and mass spectroscopy. (m+H)$^+$=338.

EXAMPLE 3

(8-Chloro-5H-dibenzo[b,e][1,4]diazepin-11-yl)-(2-pyridin-3-yl-ethyl)-amine

A solution of 0.5 g (1.9 mmol) of 8-chloro-5,10-dihydro-dibenzo[b,e][1,4]diazepin-11-thione in 10 mL of 2-ethoxyethanol was treated with 0.46 g (3.8 mmol) of 3-(2-aminoethyl)pyridine and heated at reflux overnight. The solvent was removed under reduced pressure and the residue taken up in EtOAc and washed five times with H$_2$O, then saturated NaCl solution. Drying over MgSO$_4$ and removal of the solvent under reduced pressure gave the crude product. Recrystallization from acetone/water gave 0.49 g (74% yield) of the product as a yellow solid, mp 195–196° C. The structure was confirmed by NMR and mass spectroscopy. (m+H)$^+$=349.

EXAMPLE 4

(8-Chloro-5H-dibenzo[b,e][1,4]diazepin-11-yl)-(2-imidazol-1-yl-ethyl)-amine

A solution of 0.6 g (2.3 mmol) of 8-chloro-5,10-dihydro-dibenzo[b,e][1,4]diazepin-11-thione in 15 mL of 2-ethoxyethanol was treated with 0.6 mL (4.6 mmol) of 1-(2-aminoethyl)imidazole and heated at reflux for 2 days. The solvent was removed under reduced pressure and the residue taken up in EtOAc and washed three times with H$_2$O, then saturated NaHCO$_3$ solution, and saturated NaCl solution. Drying over MgSO$_4$ and removal of the solvent under reduced pressure left the crude product. This was recrystallized from EtOAc/hexane using charcoal to give 0.44 g (57.1% yield) of the product as pale yellow crystals, mp 168–170° C. The structure was confirmed by NMR and mass spectroscopy. (m+H)$^+$=338.

EXAMPLE 5

(8-Chloro-5H-dibenzo[b,e][1,4]diazepin-11-yl)-(3-imidazol-1-yl-propyl)-amine

A solution of 0.6 g (2.3 mmol) of 8-chloro-5,10-dihydro-dibenzo[b,e][1,4]diazepin-11-thione in 15 mL of 2-ethoxyethanol was treated with 0.6 mL (4.6 mmol) of 1-(3-aminopropyl)imidazole and heated at reflux for 3 days. The solvent was removed under reduced pressure and the residue taken up in EtOAc and washed four times with H$_2$O, then saturated NaHCO$_3$ solution, and saturated NaCl solution. Drying over MgSO$_4$ and removal of the solvent under reduced pressure left the crude product. Trituration with EtOAc/hexane followed by recrystallization from acetone/water gave 506 mg (62.6% yield) of the pure product as a golden solid, mp 228–230° C. The structure was confirmed by NMR and mass spectroscopy. (m+H)$^+$=352.

EXAMPLE 6

(7-Chloro-5H-dibenzo[b,e][1,4]diazepin-11-yl) pyridin-3-ylmethyl-amine

A solution of 0.41 g (1.57 mmol) of 7-chloro-5,10-dihydro-dibenzo[b,e][1,4]diazepin-11-thione (Hunziker F., et al., *Helv. Chim. Acta,* 50:1588 (1967)) in 10 mL 2-ethoxyethanol was treated with 0.32 mL (3.14 mmol) of 3-(aminomethyl)pyridine and heated at reflux for 22 hours. The solvent was removed under reduced pressure and the residue mixed with EtOAc and filtered to give 0.31 g of product. The filtrate was concentrated and chromatographed on silica gel, eluting with EtOAc to give an additional 0.16 g of product. The material was combined and recrystallized from EtOAc/hexane to give 0.3 g (56.6% yield) of the product as a pale yellow solid, mp 218–220° C. The structure was confirmed by NMR and mass spectroscopy. $(m+H)^+=335$.

EXAMPLE 7

(5H-Dibenzo[b,e][1,4]diazepin-11-yl)-pyridin-3-ylmethyl-amine

A solution of 0.6 g (2.7 mmol) of 5,10-dihydro-dibenzo[b,e][1,4]diazepin-11-thione [German Patent, DE-2,306,762, C.A. 79:126533a (1973)] in 10 mL 2-ethoxyethanol was treated with 0.6 mL (5.4 mmol) of 3-(aminomethyl) pyridine and heated at reflux overnight. The solvent was removed under reduced pressure and the residue taken up in EtOAc and washed three times with $H_2O$, then saturated $NaHCO_3$ solution and saturated NaCl solution. Drying over $MgSO_4$ and removal of the solvent under reduced pressure left the crude product. Chromatography on silica gel, eluting with $CHCl_3$/MeOH (95/5) gave the product. On adding $CH_2Cl_2$, the product crystallized. There was obtained 459 mg (58.1% yield) of the pure product as a yellow solid, mp 150–152° C. The structure was confirmed by NMR and mass spectroscopy. $(m+H)^+=301$.

EXAMPLE 8

(8-Methyl-5H-dibenzo[b,e][1,4]diazepin-11-yl)-pyridin-3-ylmethyl-amine

A solution of 0.32 g (1.3 mmol) of 8-methyl-5,10-dihydro-dibenzo[b,e][1,4]diazepin-11-thione (Hunziker F., et al., *Helv. Chim. Acta,* 50:1588 (1967)) in 10 mL 2-ethoxyethanol was treated with 0.3 mL (2.9 mmol) of 3-(aminomethyl)pyridine and heated at reflux overnight. The solvent was removed under reduced pressure and the residue taken up in EtOAc and washed two times with $H_2O$, then saturated $NaHCO_3$ solution and saturated NaCl solution. Drying over $MgSO_4$ and removal of the solvent under reduced pressure left the crude product. Recrystallization from EtOAc/hexane gave 0.2 g (50% yield) of the pure product as a light yellow solid, mp 186–187° C. The structure was confirmed by NMR and mass spectroscopy. $(m+H)^+=315$.

EXAMPLE 9

(8-Methoxy-5H-dibenzo[b,e][1,4]diazepin-11-yl)-pyridin-3-ylmethyl-amine

A solution of 0.25 g (0.98 mmol) of 8-methoxy-5,10-dihydro-dibenzo[b,e][1,4]diazepin-11-thione (Hunziker F., et al., *Helv. Chim. Acta,* 50:1588 (1967)) in 10 mL of 2-ethoxyethanol was treated with 0.22 mL (2.1 mmol) of 3-(aminomethyl)pyridine and heated at reflux overnight. The solvent was removed under reduced pressure and the residue taken up in EtOAc and washed three times with $H_2O$, then saturated $NaHCO_3$ solution and saturated NaCl solution. Drying over $MgSO_4$ and removal of the solvent under reduced pressure left the crude product. Chromatography on silica gel, eluting with a gradient of $CH_2Cl_2$/hexane (80/20) to $CH_2Cl_2$/MeOH (94/6) gave 80 mg (25% yield) of the product as a yellow solid, mp 160–161° C. The structure was confirmed by NMR and mass spectroscopy. $(m+H)^+=331$.

EXAMPLE 10

(8-Bromo-5H-dibenzo[b,e][1,4]diazepin-11-yl)-pyridin-3-ylmethyl-amine

A solution of 0.4 g (1.3 mmol) of 8-bromo-5,10-dihydro-dibenzo[b,e][1,4]diazepin-11-thione (Sahni, S., et al., *J. Indian Chem. Soc.,* 56:625 (1979)) in 10 mL of 2-ethoxyethanol was treated with 0.28 mL (2.1 mmol) of 3-(aminomethyl)-pyridine and heated at reflux overnight. The solvent was removed under reduced pressure and the residue taken up in EtOAc and washed three times with $H_2O$, then saturated $NaHCO_3$ solution and saturated NaCl solution. Drying over $MgSO_4$ and removal of the solvent under reduced pressure left the crude product. Trituration with $CH_2Cl_2$/hexane, then with $Et_2O$/hexane left 0.3 g (61% yield) of the product as a yellow solid, mp 152–155° C. The structure was confirmed by NMR and mass spectroscopy. $(m+H)^+=379$.

EXAMPLE 11

(7,8-Dichloro-5H-dibenzo[b,e][1,4]diazepin-11yl)-pyridin-3-ylmethyl-amine

Step a. Preparation of: 7,8-Dichloro-10,11-dihydro-5H-dibenzo[b,e]-1,4-diazepin-11-thione A solution of 492 mg (1.8 mmol) of 7,8-dichloro-5,10-dihydro-dibenzo[b,e][1,4]diazepin-11-one (Giani R. P., et al., *Synthesis,* 550 (1985)) in 7 mL pyridine was treated with 0.9 g (2.1 mmol) of Lawesson's Reagent and heated at reflux overnight. The solvent was removed under reduced pressure. The residue was mixed with dilute HCl and a little acetone, then diluted with EtOAc. The EtOAc was washed with 1N HCl, $H_2O$, saturated $NaHCO_3$ solution, and saturated NaCl solution. Drying over $MgSO_4$ and removal of the solvent under reduced pressure left the crude product. This was taken up in EtOAc, treated with charcoal, filtered, and the solvent removed under reduced pressure. The residue was recrystallized from acetone/$H_2O$ to give 329 mg (63.3% yield) of a yellow solid, mp 235–260° C. (d). The structure was confirmed by mass spectroscopy. $(m+H)^+=296$.

Step b. Preparation of: (7,8-Dichloro-5H-dibenzo[b,e][1,4]diazepin-11-yl)-pyridin-3-ylmethyl-amine A solution of 329 mg (1.1 mmol) of 7,8-dichloro-5,10-dihydro-dibenzo[b,e][1,4]diazepin-11-thione in 10 mL of 2-ethoxyethanol was treated with 0.3 mL (2.2 mmol) of 3-(aminomethyl)pyridine and heated at reflux overnight. The solvent was removed under reduced pressure and the residue taken up in EtOAc and washed three times with $H_2O$, then saturated $NaHCO_3$ solution and saturated NaCl solution. Drying over $MgSO_4$ and removal of the solvent under reduced pressure left the crude product. Chromatography on silica gel, eluting with $CHCl_3$/MeOH (97/3) followed by recrystallization from acetone/$H_2O$ gave 217 mg (52.8% yield) of the product as a yellow solid, mp 209–210° C. The structure was confirmed by NMR and mass spectroscopy. $(m+H)^+=370$.

EXAMPLE 12

(8-Benzyloxy-5H-dibenzo[b,e][1,4]diazepin-11-yl)-pyridin-3-ylmethyl-amine

Step a. Preparation of: N-(2-Nitro-4-benzyloxyphenyl) anthranilic acid

Under nitrogen, a solution of 5.5 g (16.1 mmol) of diphenyliodonium-2-carboxylate, monohydrate, 3.6 g (14.6 mmol) of 2-nitro-4-benzyloxyaniline, and 0.4 g Cu(OAc)$_2$ in 50 mL of isopropanol was heated at reflux overnight. The mixture was poured into H$_2$O and acidified with dilute HCl. The solid was collected, taken up in EtOAc, and treated with charcoal. The solvent was removed under reduced pressure and the residue recrystallized from EtOAc/hexane to give 2.19 g (41.3% yield) of the product as a red-brown solid, mp 227–229° C. (d). The structure was confirmed by mass spectroscopy. (m+H)$^+$=365.

Step b. Preparation of: N-(2-Amino-4-benzyloxyphenyl) anthranilic acid

A solution of 2.17 g (6.0 mmol) of N-(2-nitro-4-benzyloxyphenyl)anthranilic acid in 100 mL THF was treated with 1.5 g Raney nickel and reduced with hydrogen at 25° C., 50 psi. The mixture was filtered and the solvent removed under reduced pressure leaving 1.95 g (97.9% yield) of the product as a tan solid. The structure was confirmed by mass spectroscopy. (m+H)$^+$=335.

Step c. Preparation of: 8-Benzyloxy-5,10-dihydro-dibenzo[b,e][1,4]diazepin-11-one A solution of 1.95 g (5.8 mmol) of N-(2-amino-4-benzyloxyphenyl)anthranilic acid in 75 mL DMF was treated with 1.6 mL (7.0 mmol) of diphenylphosphoryl azide and 1.8 mL (12.8 mmol) of Et$_3$N and allowed to stir at room temperature overnight. The solution was diluted with H$_2$O and the pH brought to Congo red end point with dilute HCl. The mixture was extracted twice with EtOAc and the combined EtOAc washed three times with H$_2$O, then saturated NaHCO$_3$ solution and saturated NaCl solution. Drying over MgSO$_4$ and removal of the solvent under reduced pressure left a dark oil. Chromatography on silica gel, eluting with CHCl$_3$, gave the product. Recrystallization from acetone/H$_2$O gave 1.19 g (64.7% yield) of the pure product as an orange solid, mp 154–156° C. The structure was confirmed by NMR and mass spectroscopy. (m+H)$^+$=317.

Step d. Preparation of: 8-Benzyloxy-5,10-dihydro-dibenzo[b,e][1,4]diazepin-11-thione A solution of 1.17 g (3.7 mmol) of 8-benzyloxy-5,10-dihydro-dibenzo[b,e][1,4]diazepin-11-one in 15 mL pyridine was treated with 1.8 g (4.4 mmol) of Lawesson's Reagent and heated at reflux overnight. The solvent was removed under reduced pressure and the residue mixed with dilute HCl and a little acetone. The mixture was diluted with EtOAc and washed with 1N HCl, H$_2$O, saturated NaHCO$_3$ solution, and saturated NaCl solution. Drying over MgSO$_4$ and removal of the solvent under reduced pressure left the crude product. This was taken up in EtOAc, treated with charcoal, and the solvent removed under reduced pressure. The residue was recrystallized from acetone/H$_2$O to give 0.95 g (77.9% yield) of the product as a golden solid, mp 203–205° C. The structure was confirmed by mass spectroscopy. (m+H)$^+$=333.

Step e. Preparation of: 8-Benzyloxy-5H-dibenzo [b,e][1,4]diazepin-11-yl)-pyridin-3-ylmethyl-amine A solution of 0.6 g (1.8 mmol) of 8-benzyloxy-5,10-dihydro-dibenzo[b,e][1,4]diazepin-11-thione in 10 mL 2-ethoxyethanol was treated with 0.4 mL (3.6 mmol) of 3-(aminomethyl)pyridine and heated at reflux overnight. The solvent was removed under reduced pressure and the residue taken up in EtOAc and washed three times with H$_2$O, then with saturated NaHCO$_3$ solution and saturated NaCl solution. Drying over MgSO$_4$ and removal of the solvent under reduced pressure gave the crude product. After trituration with CHCl$_3$/hexane, recrystallization from MeOH gave 349 mg (47.8% yield) of the product as a yellow solid, mp 196–197° C. The structure was confirmed by NMR and mass spectroscopy. (m+H)$^+$=407.

EXAMPLE 13

(7,8-Dichloro-2,3-dimethoxy-5H-dibenzo[b,e][1,4]diazepin-11-yl)-pyridin-3-ylmethyl-amine Step a. Preparation of: 2-(2-Amino-4,5-dichlorophenylamino)-4,5-dimethoxy-benzoic acid Under nitrogen, a solution of 5.36 g (16.2 mmol) of 2-iodo-4,5-dimethoxybenzoic acid, sodium salt in 50 mL DMF was treated with 2.9 g (16.2 mmol) of 2-amino-4,5-dichloroaniline, 0.2 g Cu(OAc)$_2$, and 1.8 mL (16.2 mmol) of N-methylmorpholine and heated at reflux for 4 hours. The mixture was poured into H$_2$O and acidified with 16.2 mL (32.4 mmol) of 2N HCl. The mixture was extracted with EtOAc and the EtOAc washed three times with H$_2$O, then with saturated NaCl solution. Drying over MgSO$_4$ and removal of the solvent under reduced pressure left the crude product as a black oil. Mixing with CH$_2$Cl$_2$/hexane gave a solid which was recrystallized from acetone/H$_2$O to give 596 mg (11.7% yield) of a yellow solid, mp 210–212° C. (d). The structure was confirmed by mass spectroscopy. (m+H)$^+$=358.

Step b. Preparation of: 7,8-Dichloro-2,3-dimethoxy-5,10-dihydro-dibenzo[b,e][1,4]diazepin-11-one A solution of 595 mg (1.7 mmol) of 2-(2-amino-4,5-dichlorophenylamino)-4,5-dimethoxy-benzoic acid in 20 mL DMF was treated with 0.6 mL (3.7 mmol) of Et$_3$N and 0.42 mL (2.0 mmol) of diphenylphosphoryl azide and allowed to stir at room temperature overnight. The solution was poured into H$_2$O and acidified to the Congo red end point with dilute HCl. A solid was collected which was triturated with CH$_3$CN/MeOH to give 359 mg (64.1% yield) of the product as a pale yellow solid, mp 297–300° C. (d). The structure was confirmed by mass spectroscopy. (m+H)$^+$=340.

Step c. Preparation of: 7,8-Dichloro-2,3-dimethoxy-5,10-dihydro-dibenzo[b,e][1,4]diazepin-11thione A solution of 359 mg (1.1 mmol) of 7,8-dichloro-2,3-dimethoxy-5,10-dihydro-dibenzo[b,e][1,4]diazepin-11-one in 10 mL pyridine was treated with 0.53 g (1.3 mmol) of Lawesson's Reagent and heated at reflux overnight. The solvent was removed under reduced pressure and the residue mixed with dilute HCl and a little acetone. The mixture was diluted with EtOAc and washed with 1N HCl, two times with H$_2$O, saturated NaHCO$_3$ solution, and saturated NaCl solution. Drying over MgSO$_4$ and removal of the solvent under reduced pressure gave the crude product. Trituration with CH$_2$Cl$_2$/hexane gave 305 mg (82.4% yield) of the product as an orange solid, mp 279–281° C. (d). The structure was confirmed by mass spectroscopy. (m+H)$^+$=356.

Step d. Preparation of: 7,8-Dichloro-2,3-dimethoxy-5H-dibenzo[b,e][1,4]diazepin-11-yl)-pyridin-3-ylmethyl-amine A solution of 302 mg (0.9 mmol) of 7,8-dichloro-2,3-dimethoxy-5,10-dihydro[b,e][1,4]diazepin-11-thione in 15 mL of 2-ethoxyethanol was treated with 0.36 mL (3.6 mmol) of 3-(aminomethyl)pyridine and heated at reflux for 3 days. The solvent was removed under reduced pressure and the residue taken up in EtOAc and washed three times with H$_2$O, then with saturated NaHCO$_3$ solution and saturated NaCl solution. Drying over MgSO$_4$ and removal of the solvent under reduced pressure left the crude product. Chromatography on silica gel, eluting with CHCl$_3$/MeOH (95/5) gave 250 mg (69.4% yield) of the product as a golden solid foam. The structure was confirmed by NMR and mass spectroscopy. (m+H)$^+$=430.

EXAMPLE 14

(11H-Benzo[b]pyrido[2,3-e][1,4]diazepin-5-yl)-pyridin-3-ylmethyl-amine

A solution of 0.5 g (2.2 mmol) of 6,11-dihydro-5H-pyrido[2,3-b][1,5]benzodiazepin-5-thione [(European Published Patent Application EP-393,604); C.A. 114, 143455] in 10 mL 2-ethoxyethanol was treated with 0.24 mL (10.8 mmol) of 3-(aminomethyl)pyridine and heated at reflux for 2 days. The mixture was poured into $H_2O$ and extracted with EtOAc. The EtOAc was washed three times with $H_2O$, then saturated $NaHCO_3$ solution and saturated NaCl solution. Drying over $MgSO_4$ and removal of the solvent under reduced pressure left the crude product. Chromatography on silica gel, eluting with a gradient of $CH_2Cl_2$/hexane (90/10) to $CH_2Cl_2$/MeOH (94/6) gave 0.35 g (53% yield) of the product as a yellow solid, mp 192–194° C. The structure was confirmed by NMR and mass spectroscopy. $(m+H)^+$=302.

EXAMPLE 15

(8-Chloro-5-methyl-5H-dibenzo[b,e][1,4]diazepin-11-yl)-pyridin-3-ylmethyl-amine

A solution of 329 mg (1.2 mmol) of 8-chloro-5-methyl-5,10-dihydro-dibenzo[b,e][1,4]diazepin-11-thione (Hunziker F., et al., *Helv. Chim. Acta*, 50:1588 (1967)) in 10 mL of 2-ethoxyethanol was treated with 0.3 mL (2.4 mmol) of 3-(aminomethyl)pyridine and heated at reflux overnight. The solvent was removed under reduced pressure and the residue taken up in EtOAc and washed three times with $H_2O$, then saturated $NaHCO_3$ solution and saturated NaCl solution. Drying over $MgSO_4$ and removal of the solvent under reduced pressure left the crude product as an oil. Chromatography on silica gel, eluting with $CHCl_3$/MeOH (98/2) gave 160 mg (38.4% yield) of the product as a golden solid foam. The structure was confirmed by NMR and mass spectroscopy. $(m+H)^+$=349.

EXAMPLE 16

(8-Chloro-dibenzo[b,f][1,4]thiazepin-11-yl-pyridin-3-ylmethyl-amine

A solution of 682 mg (2.5 mmol) of 8-chlorodibenzo[b,f]-1,4-thiazepin-11(10H)-thione (Polivka Z., et al., *Coll. Czech. Chem. Comm.*, 48:1465 (1983)) in 15 mL of 2-ethoxyethanol was treated with 0.5 mL (5.0 mmol) of 3-(aminomethyl)pyridine and heated at reflux overnight. The solvent was removed under reduced pressure and the residue taken up in EtOAc and washed three times with $H_2O$, then saturated $NaHCO_3$ solution and saturated NaCl solution. Drying over $MgSO_4$ and removal of the solvent under reduced pressure left the crude product. Chromatography on silica gel, eluting with $CHCl_3$/MeOH (98/2) following by recrystallization from $CHCl_3$/hexane gave 600 mg (69.8% yield) of the product as a white solid, mp 152–153° C. The structure was confirmed by NMR and mass spectroscopy. $(m+H)^+$=352.

EXAMPLE 17

(8-Chloro-5,5-dioxo-5H-5$\lambda^6$-dibenzo[b,f][1,4]thiazepin-11-yl)-pyridin-3-ylmethyl-amine Step a. Preparation of: 8-Chloro-5,5-dioxo-dibenzo[b,f]-1,4-thiazepin-11(10H)-one A suspension of 0.91 g (3.5 mmol) of 8-chloro dibenzo[b,f]-1,4-thiazepin-11(10H)-one in 100 mL HOAc was warmed to 90° C. to effect solution, and the hot solution was treated over 2 hours with 10 mL of 30% $H_2O_2$. The solution was then allowed to stand at room temperature for 3 days. A solid separated and was washed with $H_2O$ to give 526 mg (51.6% yield) of the product, mp >300° C. The structure was confirmed by mass spectroscopy. $(m+H)^+$=294.

Step b. Preparation of: 8-Chloro-5,5-dioxo-dibenzo[b,f]-1,4-thiazepin-11(10H)-thione A solution of 507 mg (1.7 mmol) of 8-chloro-5,5-dioxo-dibenzo[b,f]-1,4-thiazepin-11(10H)-one in 15 mL pyridine was treated with 0.88 g (2.1 mmol) of Lawesson's Reagent and heated at reflux overnight. The solvent was removed under reduced pressure and the residue treated with dilute HCl and a little acetone. The material was taken up in EtOAc and washed with 1N HCl, two times with $H_2O$, saturated $NaHCO_3$ solution, and saturated NaCl solution. Drying over $MgSO_4$ and removal of the solvent under reduced pressure gave the crude product. Since thin layer chromatography showed a mixture of product and starting material, the crude product was re-treated with Lawesson's Reagent and refluxed for 3 days. Work-up as above gave 0.46 g (86.8% yield) of the product as a golden solid, mp 255–260° C. (d). The structure was confirmed by mass spectroscopy. $(m+H)^+$=310.

Step c. Preparation of: (8-Chloro-5,5-dioxo-5H-5$\lambda^6$-dibenzo[b,f][1,4]thiazepin-11-yl)-pyridin-3-ylmethyl-amine A solution of 0.46 g (1.5 mmol) of 8-chloro-5,5-dioxo-dibenzo[b,f]-1,4-thiazepin-11(10H)-thione in 15 mL of 2-ethoxyethanol was treated with 0.3 mL (3.0 mmol) of 3-(aminomethyl)pyridine and heated at reflux overnight. An additional 0.4 mL of 3-(aminomethyl)pyridine was added and the refluxing continued another night. The solvent was removed under reduced pressure and the residue taken up in EtOAc and washed three times with $H_2O$, then saturated $NaHCO_3$ solution and saturated NaCl solution. Drying over $MgSO_4$ and removal of the solvent under reduced pressure left the crude product. Chromatography on silica gel, eluting with $CHCl_3$/MeOH (97/3) followed by precipitating the product from acetone with $H_2O$ gave an amorphous tan solid. The structure was confirmed by NMR and mass spectroscopy. $(m+H)^+$=384.

EXAMPLE 18

(8-Chloro-dibenzo[b,f][1,4]oxazepin-11-yl)-pyridin-3-ylmethyl-amine

A solution of 706 mg (2.7 mmol) of 8-chlorodibenzo[b,f]-1,4-oxazepin-11(10H)-thione (Nagarajan K., et al., *Indian J. Chem.*, 12:258 (1974)) in 20 mL of 2-ethoxyethanol was treated with 0.6 mL (5.4 mmol) of 3-(aminomethyl)pyridine and heated at reflux overnight. The solvent was removed under reduced pressure and the residue taken up in EtOAc and washed three times with $H_2O$, then saturated $NaHCO_3$ solution and saturated NaCl solution. Drying over $MgSO_4$ and removal of the solvent under reduced pressure left the crude product. Chromatography on silica gel, eluting with $CHCl_3$/MeOH (98/2) followed by recrystallization from $CH_2Cl_2$/hexane gave 436 mg (48.1% yield) of the product as a cream solid, mp 167–169° C. The structure was confirmed by NMR and mass spectroscopy. $(m+H)^+$=336.

We claim:

1. A compound of Formula I

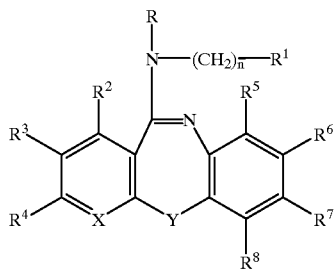

wherein X is C—$R^9$, wherein $R^9$ is as defined hereinafter or N;

Y is

wherein $R^{10}$ is hydrogen, alkyl, or substituted alkyl wherein the substituent on the alkyl group is selected from the group consisting of:

$OR^{11}$ wherein $R^{11}$ is hydrogen, or alkyl, $SR^{11}$ wherein $R^{11}$ is as defined above, $CO_2R^{12}$ wherein $R^{12}$ is hydrogen, alkyl, or benzyl,

wherein $R^{13}$ and $R^{14}$ are independently the same or different and each is hydrogen, alkyl, or $R^{13}$ and $R^{14}$ are taken together with N to form a 5- or 6-membered ring optionally containing a heteroatom selected from the group consisting of N, S, and O, or

wherein $R^{13}$ and $R^{14}$ are as defined above, —$CH_2$—, —O—, —$S(O)_m$— wherein m is zero or an integer of 1 or 2,

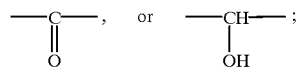

or

R is hydrogen, or alkyl;

n is an integer of 1 to 5;

$R^1$ is heteroaryl;

$R^2$, $R^3$, $R^4$, $R^5$, $R^6$, $R^7$, $R^8$, and $R^9$ are each independently the same or different and each is hydrogen, $NO_2$,

wherein $R^{13}$ and $R^{14}$ are as defined above,

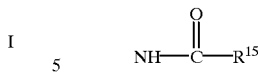

wherein $R^{15}$ is hydrogen, alkyl, or aryl, $CO_2R^{12}$ wherein $R^{12}$ is as defined above,

wherein $R^{13}$ and $R^{14}$ are as defined above,

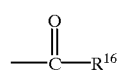

wherein $R^{16}$ is alkyl, aryl, or arylalkyl, halogen, CN, OH, $SR^{17}$ wherein $R^{17}$ is hydrogen, or alkyl, SO alkyl, $SO_2$ alkyl, alkoxy, benzyloxy, alkyl, or substituted alkyl wherein the substituents on the alkyl group are as defined above;

with the proviso that at least two of $R^2$, $R^3$, $R^4$, or $R^9$ are hydrogen and at least one of $R^5$, $R^6$, $R^7$, or $R^8$ is hydrogen; and corresponding isomers thereof;

or a pharmaceutically acceptable salt thereof.

2. A compound according to claim 1 wherein $R^1$ is a heteroaryl radical selected from the group consisting of:

2- or 3-thienyl;

2- or 3-furanyl;

1-, 2-, or 3-pyrrolyl;

1-, 2-, 4-, or 5-imidazolyl;

1-, 3-, 4-, or 5-pyrazolyl;

2-, 4-, or 5-thiazolyl;

3-, 4-, or 5-isothiazolyl;

2-, 4-, or 5-oxazolyl;

3-, 4-, or 5-isoxazolyl;

1-, 2-, 4-, or 5-1,2,3-triazolyl;

1- or 5-tetrazolyl;

4- or 5-1,2,3-oxadiazolyl;

3- or 5-1,2,4-oxadiazolyl;

2-1,3,4-oxadiazolyl;

2-1,3,4-thiadiazoyl;

2-1,3,5-triazinyl;

3-pyridinyl;

3-, 4-, or 5-pyridazinyl;

2-pyrazinyl; and

2-, 4-, or 5-pyrimidinyl; or optionally, the heteroaryl radical is substituted with a substituent selected from the group consisting of:

$NH_2$,

OH,

SH, halogen, alkyl, or alkoxy.

3. A compound according to claim 2 wherein Y is —NH—,

—N(alkyl)—,

—O—,
—S—, or
—SO₂—;

n is an integer of 1 to 5;
R¹ is a heteroaryl radical selected from the group consisting of:
- 1-, 2-, or 4-imidazolyl,
- 3-pyridinyl,
- 1-, 3-, or 5-1,2,4-triazolyl,
- 5-thiazolyl, or
- 5-oxazolyl;

R³ and R⁴ are hydrogen or alkoxy;
R⁶ and R⁷ are
- hydrogen,
- halogen,
- mercaptomethyl,
- hydroxymethyl,
- alkoxy,
- alkyl, or
- benzyloxy.

4. A compound according to claim 3 selected from the group consisting of:
(8-Chloro-5H-dibenzo[b,e][1,4]diazepin-11-yl)pyridin-3-ylmethyl-amine;
(8-Chloro-5H-dibenzo[b,e][1,4]diazepin-11-yl)-[2-(3H-imidazol-4-yl)-ethyl]-amine;
(8-Chloro-5H-dibenzo[b,e][1,4]diazepin-11-yl)-(2-pyridin-3-yl-ethyl)-amine;
(8-Chloro-5H-dibenzo[b,e][1,4]diazepin-11-yl)-(2-imidazol-1-yl-ethyl)-amine;
(8-Chloro-5H-dibenzo[b,e][1,4]diazepin-11-yl)-(3-imidazol-1-yl-propyl)-amine;
(7-Chloro-5H-dibenzo[b,e][1,4]diazepin-11-yl)-pyridin-3-ylmethyl-amine;
(5H-Dibenzo[b,e][1,4]diazepin-11-yl)-pyridin-3-ylmethyl-amine;
(8-Methyl-5H-dibenzo[b,e][1,4]diazepin-11-yl)-pyridin-3-ylmethyl-amine;
(8-Methoxy-5H-dibenzo[b,e][1,4]diazepin-11-yl)-pyridin-3-ylmethyl-amine;
(8-Bromo-5H-dibenzo[b,e][1,4]diazepin-11-yl)-pyridin-3-ylmethyl-amine;
(7,8-Dichloro-5H-dibenzo[b,e][1,4]diazepin-11-yl)-pyridin-3-ylmethyl-amine;
(8-Benzyloxy-5H-dibenzo[b,e][1,4]diazepin-11-yl)-pyridin-3-ylmethyl-amine;
(7,8-Dichloro-2,3-dimethoxy-5H-dibenzo[b,e][1,4]diazepin-11-yl)-pyridin-3-ylmethyl-amine;
(11H-Benzo[b]pyrido[2,3-e][1,4]diazepin-5-yl)-pyridin-3-ylmethyl-amine;
(8-Chloro-5-methyl-5H-dibenzo[b,e][1,4]diazepin-11yl)-pyridin-3-ylmethyl-amine;
(8-Chloro-dibenzo[b,f][1,4]thiazepin-11-yl)-pyridin-3-ylmethyl-amine;
(8-Chloro-5,5-dioxo-5H-5λ⁶-dibenzo[b,f][1,4]thiazepin-11-yl)-pyridin-3-ylmethyl-amine; and
(8-Chloro-dibenzo[b,f][1,4]oxazepin-11-yl)-pyridin-3-ylmethyl-amine.

5. A method of treating tissue proliferative diseases comprising administering to a host suffering therefrom a therapeutically effective amount of a compound according to claim 1 in unit dosage form.

6. A method of treating ras-related cancer comprising administering to a host suffering therefrom a therapeutically effective amount of a compound according to claim 1 in unit dosage form.

7. A method of treating restenosis comprising administering to a host suffering therefrom a therapeutically effective amount of a compound according to claim 1 in unit dosage form.

8. A method of treating psoriasis comprising administering to a host suffering therefrom a therapeutically effective amount of a compound according to claim 1 in unit dosage form.

9. A method of treating prenyl-related viral infections comprising administering to a host suffering therefrom a therapeutically effective amount of a compound according to claim 1 in unit dosage form.

10. A pharmaceutical composition comprising a compound according to claim 1 in admixture with a pharmaceutically acceptable excipient, diluent, or carrier.

11. A pharmaceutical composition adapted for administration as an antiproliferative agent comprising a therapeutically effective amount of a compound according to claim 1 in admixture with a pharmaceutically acceptable excipient, diluent, or carrier.

12. A pharmaceutical composition adapted for administration as an anticancer agent, or restenosis inhibiting agent or antipsoriasis agent or antiviral agent comprising a therapeutically effective amount of a compound according to claim 1 in admixture with a pharmaceutically acceptable excipient, diluent, or carrier.

13. A method for preparing a compound having the Formula Ia

Ia wherein X is C—R⁹ wherein R⁹ is as defined hereinafter or N;

R is hydrogen, or alkyl;

n is an integer of 1 to 5;

R¹ is heteroaryl;

R², R³, R⁴, R⁵, R⁶, R⁷, R⁸, and R⁹ are each independently the same or different and each is hydrogen, NO₂,

N(R¹³)(R¹⁴)

wherein R¹³ and R¹⁴ are independently the same or different and each is hydrogen, alkyl, or R¹³ and R¹⁴ are taken together with N to form a 5- or 6-membered ring optionally containing a heteroatom selected from the group consisting of N, S, and O,

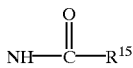

wherein $R^{15}$ is hydrogen, alkyl, or aryl, $CO_2R^{12}$ wherein $R^{12}$ is hydrogen, alkyl, or benzyl,

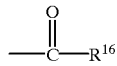

wherein $R^{13}$ and $R^{14}$ are as defined above,

wherein $R^{16}$ is alkyl, aryl, or arylalkyl, halogen, CN, OH, $SR^{17}$ wherein $R^{17}$ is hydrogen, or alkyl, SO alkyl, $SO_2$ alkyl, alkoxy, benzyloxy, alkyl, or substituted alkyl wherein the substituent on the alkyl group is selected from the group consisting of:

$OR^{11}$ wherein $R^{11}$ is hydrogen, or alkyl, $SR^{11}$ wherein $R^{11}$ is as defined above, $CO_2R^{12}$ wherein $R^{12}$ is hydrogen, alkyl, or benzyl,

wherein $R^{13}$ and $R^{14}$ are as defined above, or

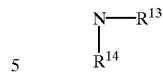

wherein $R^{13}$ and $R^{14}$ are as defined above;

with the proviso that at least two of $R^2$, $R^3$, $R^4$, or $R^9$ are hydrogen and at least one of $R^5$, $R^6$, $R^7$, or $R^8$ is hydrogen; and corresponding isomers thereof; or a pharmaceutically acceptable salt thereof comprises reaction of a compound of Formula II

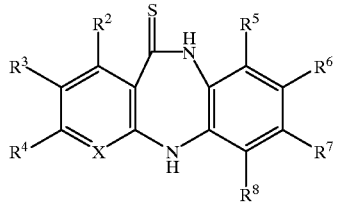

wherein X, $R^2$, $R^3$, $R^4$, $R^5$, $R^6$, $R^7$, and $R^8$ are as defined above with a compound of Formula III

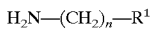

$H_2N-(CH_2)_n-R^1$  III wherein n and $R^1$ are as defined above in a solvent to afford a compound of Formula 1a and, if desired, converting a compound of Formula Ia to a corresponding pharmaceutically acceptable salt by conventional means and, if so desired, converting the corresponding pharmaceutically acceptable salt to a compound of Formula Ia by conventional means.

* * * * *